US011697820B2

(12) United States Patent
Witek et al.

(10) Patent No.: US 11,697,820 B2
(45) Date of Patent: Jul. 11, 2023

(54) **LATE BLIGHT RESISTANCE GENE FROM *SOLANUM AMERICANUM* AND METHODS OF USE**

(71) Applicant: TWO BLADES FOUNDATION, Evanston, IL (US)

(72) Inventors: Kamil Witek, Norwich (GB); Jonathan D. G. Jones, Norfolk (GB)

(73) Assignee: Two Blades Foundation, Evanston, IL (US)

( * ) Notice: Subject to any disclaimer, the term of this patent is extended or adjusted under 35 U.S.C. 154(b) by 150 days.

(21) Appl. No.: 15/572,627

(22) PCT Filed: May 6, 2016

(86) PCT No.: PCT/US2016/031119
§ 371 (c)(1),
(2) Date: Nov. 8, 2017

(87) PCT Pub. No.: WO2016/182881
PCT Pub. Date: Nov. 17, 2016

(65) Prior Publication Data
US 2018/0142254 A1 May 24, 2018

Related U.S. Application Data

(60) Provisional application No. 62/159,240, filed on May 9, 2015.

(51) Int. Cl.
*C12N 15/82* (2006.01)
*A23K 10/30* (2016.01)
*A23L 19/00* (2016.01)
*C12Q 1/6895* (2018.01)

(52) U.S. Cl.
CPC .......... *C12N 15/8282* (2013.01); *A23K 10/30* (2016.05); *A23L 19/00* (2016.08); *C12N 15/8261* (2013.01); *C12Q 1/6895* (2013.01); *A23V 2002/00* (2013.01); *C12Q 2600/13* (2013.01); *C12Q 2600/158* (2013.01); *Y02A 40/146* (2018.01)

(58) Field of Classification Search
CPC .................................................. C12N 15/8282
See application file for complete search history.

(56) References Cited

U.S. PATENT DOCUMENTS

2010/0192257 A1* 7/2010 Jones ................. C12N 15/8282 800/279

FOREIGN PATENT DOCUMENTS

WO 2009013468 A2 1/2009
WO 2013009935 A2 1/2013

OTHER PUBLICATIONS

Jupe et al, The Plant J. (2013) 76:530-544.*
Melo et al., Plant Syst. Evol. (2011) 293:227-235.*
Ristaino et al, Ann. Rev. Phytopathol. (2000) 38:541-76.*
Fry, W., Mol. Plant Path. (2008) 9:385-402.*
Ballvora et al, Plant J. (2002) 30:361-371.*
Jupe et al, Plant J. (2013) 76:530-544.*
Lebecka, Eur. J. Plant Pathol. (2009) 124:345-348.*
Lebecka, R., "Host-pathogen interaction between Phytophthora infestans and Solanum nigrum, S. villosum, and S. scabrum," European Journal of Plant Pathology, Kluwer Academic Publishers, vol. 120, No. 3, pp. 233-240, Sep. 19, 2007.
Florian, Jupe, et al., "Resistance gene enrichment sequencing (RenSeq) enables reannotation of the NB-LRR gene family from sequenced plant genomes and rapid mapping of resistance loci in segregating populations," The Plant Journal, vol. 76, No. 3, pp. 530-544, Oct. 8, 2013.
Campos, M.A., et al., "Putative pathogenesis-related genes within *Solanum nigrum* L. var. americanum genome: isolation of two genes coding for PR5-like proteins, phylogenetic and sequence analysis," Physiological and Molecular Plant Pathology, vol. 61, No. 4, pp. 205-216, Oct. 1, 2002.
Lebecka, R., "Inheritance of resistance in Solanum nigrum to Phytophthora infestans," European Journal of Plant Pathology, Kluwer Academic Publishers, vol. 124, No. 2, pp. 345-348, Jan. 13, 2009.
Zossen Van Der, E. et al., "An ancient R gene from the wild potato species *Solanum bulbocastanum* confers broad-spectrum resistance to Phytophthora infestans in cultivated potato and tomato," The Plant Journal, Blackwell Scientific Publications, vol. 36, No. 6, pp. 867-882, Dec. 1, 2003.
Witek, Kamil., et al., "Accelerated cloning of a potato late blight-resistance gene using RenSeq and SMRT sequencing," Nature Biotechnology, vol. 34, No. 6, pp. 656-660, Apr. 25, 2016.
International Search Report and Written Opinion for PCT/US2016/031119, EPO, dated Jul. 5, 2016.
Golas, T.M., European *Solanum dulcamara* L. and its interaction with Phytophthora infestans (Mont.) de Bary, 2010, Ph.D. dissertation, Radboud Univesity, Nijmegen, NL, 131 pp.
Qi, D. & Innes, R.W., "Recent advances in plant NLR structure, function, localization and signaling," Frontiers in Immunology, vol. 4, No. 348, pp. 1-10, Oct. 21, 2013.

(Continued)

*Primary Examiner* — Mykola V. Kovalenko
(74) *Attorney, Agent, or Firm* — Williams Mullen; David M. Saravitz

(57) ABSTRACT

Compositions and methods and for enhancing the resistance of plants to a plant disease caused by a *Phytophthora* species are provided. The compositions comprise nucleic acid molecules encoding resistance (R) gene products and variants thereof and plants, seeds, and plant cells comprising such nucleic acid molecules. The methods for enhancing the resistance of a plant to a plant disease caused by a *Phytophthora* species comprise introducing a nucleic acid molecule encoding an R gene product into a plant cell. Additionally provided are methods for using the plants in agriculture to limit plant disease.

10 Claims, 7 Drawing Sheets

Figure 1:
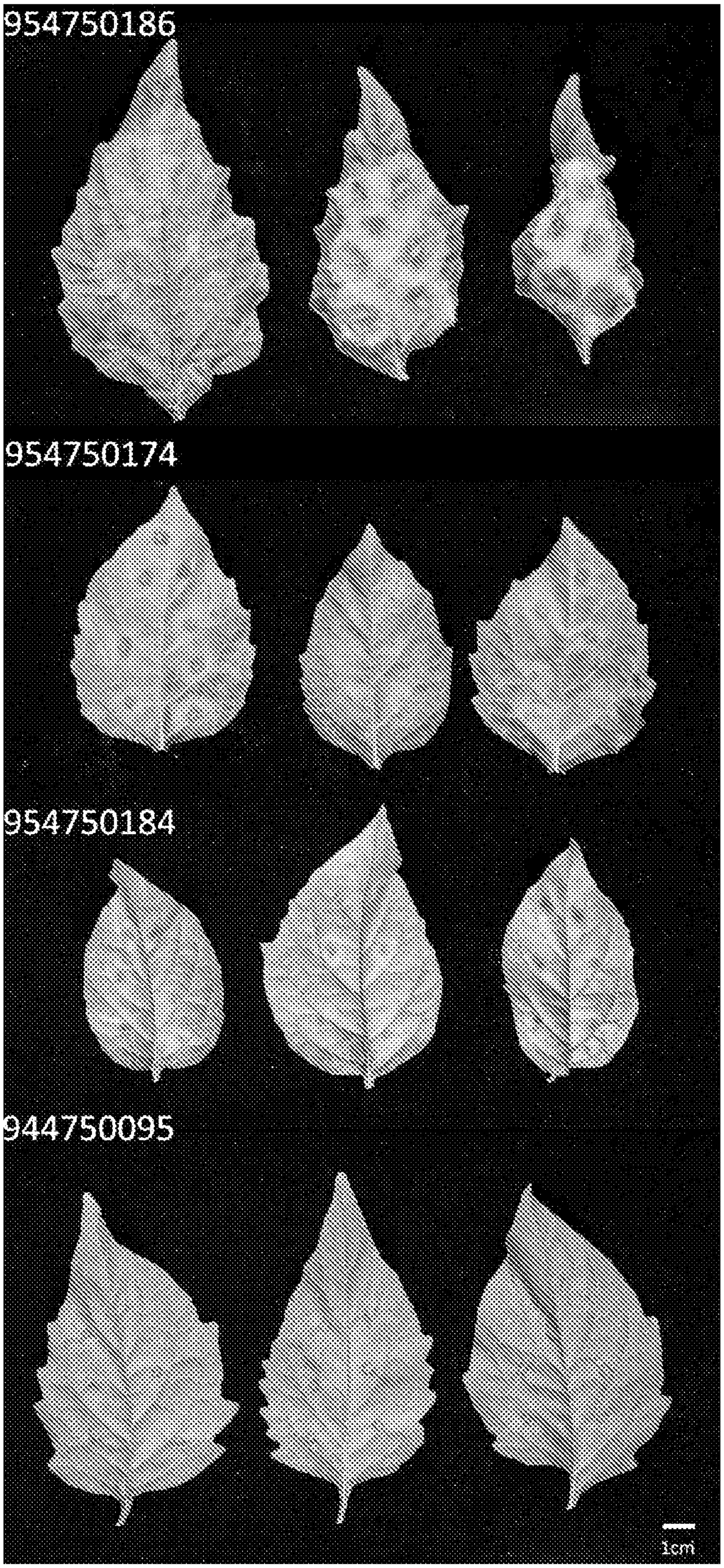

Specification includes a Sequence Listing.

(56) References Cited

OTHER PUBLICATIONS

Becktell, M.C., et al., "Host-Pathogen Interactions Between Phytophthora infestans and the Solanaceous Hoste Calibrachoa x hybridus. Petunia x hybrids, and Nicotians benthamiana," Plant Disease, vol. 30, No. 1, pp. 24-32, Jan. 2006.
De Araujo, A.C., et al., "Plant NLR receptor proteins and their potential in the development of durable genetic resistance to biotic stresses," Biotechnology Research and Innovation, vol. 3., pp. 80-94, Jan. 31, 2020.
Forbes, G.A. et al., "Phytophthora infestans and Phytophthora andina on solanaceous hosts in South America," In: Phytophthora: A Global Perspective, Lamour, ed., Centre for Agriculture and Bloscience International (CABI), Wallingford, UK, pp. 48-58, 2013.
Witek, K. et al.. "Accelerated cloning of a potato late blight-resistance gene using RenSeq and SMRT sequencing," Nature Biotechnology, vol. 34. No. 6, Supplementary Text and Figures, pp. 1-18, Apr. 25, 2016.

* cited by examiner

SEQUENCE LISTING

```
<160> NUMBER OF SEQ ID NOS: 3

<210> SEQ ID NO 1
<211> LENGTH: 5352
<212> TYPE: DNA
<213> ORGANISM: Solanum americanum
<220> FEATURE:
<221> NAME/KEY: promoter
<222> LOCATION: (1)..(1918)
<220> FEATURE:
<221> NAME/KEY: terminator
<222> LOCATION: (4583 )..(5352)

<400> SEQUENCE: 1

gtccatatgt ggaagctact ctctttgtcc aaaaatagtt gtccactatt gacttacaca     60

caccttaaga aataataaat aataggggta ctattactac actatccttt gaatattata    120

aatttaatgc tctgggaaaa tgtattagat attgaatact ccctccgttt caaaaagaat    180

agtctacttt gacttggcaa agagttttaa aaaataaaga aaatttttca atcttgtagt    240

tctaaattaa tgttatgtca aatgtaccaa aatatctttt aatcttgtag ccttgaacat    300

gccacgtgga aagttgaaat taaagtgttg atcaaaaagg aaagaggtca ctattttcta    360

aacggagggg tggtatttaa ttgtaggggt aaaatagaca caaaaggata aattatcttt    420

tgattttcta aattggacaa gtattgttgg acaactattt ttcgtatagt gggcaagtaa    480

agatggacgg gggaggtatt accaagtcta aaaatgggaa gctatggcca agtctaaact    540

gatactccat gtgttccttt ttatttgtca cgtttttttt tttttgagaa atcaaactac    600

atgaattttg accaatattt taagatctac tttttcaaat agttctcaaa catctaaatt    660

ttaaataata aattattcta attcaaatta gcttcaaaaa ttagtcaaat tgactttcag    720

aaagtcaatt gtgacgatta aaaaagaatg gagagagtaa gttttttttaa aatcttattc    780

tccattattt acatgacgag tcttggagaa ttttcacttt gttaaggatt cgattcttca    840

tatcgtaatc ccttccccta ttcttccttt cacctgcccc tttttgaaaa ttaaatatga    900

cccagaggct gcttttttat atattgcttc acataccccca ttttttttatt ttttattttg    960

aaaaacggaa aaagacatga cgagccccac tagtctttca ttatttctca ttttttgtac   1020

acattgaatt tctttggaat ttaataaagg tagtacttag atttgaccaa tccaaactat   1080

gtgcctttgg cgtgttgctt tttttaaaaa aattattttt tgaaactttt gataataagt   1140

tgtcacatgt gtagcatttt tgactttgat cttcaaggct tattgagggc aagtggggtc   1200

gaaaattcaa tatcaccgat ttataattgg atggggattt ttatttacat ctggcattag   1260
```

-continued

```
tcgattttga aaagaatgtc tctttcgtaa tttgagaact cgttaatcac aatattgcac   1320
atcaacagat aacatgttta agatcacaaa attaaaaaac aatttgatat attattacac   1380
atatctttag tttaacacta taagattcaa aaatcttctt tggtttctga aacttcattg   1440
tcgaatcaaa taaaaacgaa aaagttgaaa tagagagaga aaaggtagtt tccttgaaat   1500
ttctctagat ttggagcaat ccaatgtttt tctgtatcaa aattttacat attgatggtg   1560
agtactgtca ataatgtagt actccctctg tcccaattta tatgactcac tttccttttt   1620
ggtcagtccc aaaaagaatg acacatttct acatttagta acaatttatt tttaaaatga   1680
ctttttttact cttaatgaaa tgatttctag ccacacaaat atctaccact catttttagac   1740
cacaaatttc aaaagtcttc ctttctttgt taaactccgt gccgagtcaa actatgtcat   1800
ataaattggg acggagggag tatgatattt cttctctttt gagtaatatt taatatcttc   1860
aattaaatcc tatccactcc tcatctattc ttgttcatca tttttgagaa ttaatttgat   1920
ggcagcttat agtgctgtaa tttctcttct tcaaacactt attgatcaac aaaatatttc   1980
agaactcttt catggtcaca ctgcccaaac gctcgattct cttcacacta cagctgaata   2040
ttttcaacat gtccttgaaa atattacaag atttgactct gaaaagatca aatctttgga   2100
ggaaaaaata agagttgttg ttagctatgc agaagatgtt gttgcaatga aaatttctca   2160
aatcatcata ggctcaagct ggacatttgg aattttacaa caccaggatt tactaccact   2220
tgttgaaaaa atggacacaa caaagaaaca agtgatggac attctttctc atgatgatga   2280
tcaaattctt gaattaactg caggggattc cttgattggc acttcttcta caacttatcc   2340
aatgttggaa gatgatatcg tgcagggaat tgatgatgac ttggagatca tagttaaaag   2400
attgacagga ccaccacggg atttagacgt tgtcacaata acaggtatgg gtggcattgg   2460
taaaacaaca ctcgctagaa aggcttatga tcatctcaca atcaggtatc actttgacat   2520
tcttgtttgg attacaatat ctcaagaatt tcgatgtaga aatgtattgt tagaagcttt   2580
acattgcatt tcaaagtcaa cagatattgt gaacacaaaa gattatgata agaaggatga   2640
caatgagtta gctgacatag tacagaaaaa actaaagggt ccaagatacc tagttgttgt   2700
tgatgatatt tggagtagag atgtttggga tagtataaga ggaatatttc ctaattacaa   2760
caacgggagt cgaatcttat tgactactag ggaaaacgag gtagcaatgt atgcaaatac   2820
ttgtagccct catgagatga gtcttttgag tttagaaaac ggttggaggt tactttgtga   2880
taaggtgttt ggaccaaaac atgatcatcc tcctgaattg gaagaaattg gtaaggaaat   2940
agttgaaaaa tgccaaggac tacccttaac aatttcagtg attgcgggac atgtttctaa   3000
aatgcccagg acattagaat gttggaagga tgtcgcccga accttaagtg aaatcatctc   3060
tagtcatcca gataattgct taggagtgct cggtttgagt taccatcact tgcctaatca   3120
cctcaaacct tgctttcttt ctatgagtag tttcccagaa gattttcagg ttgaaactcg   3180
gagattgatc tacttatgga tcgcagaagg tttcataagg acttgcgaaa atggtaaaag   3240
tttggaggaa gttgcagtag attatttgga ggaccttatt agcaggaact tgatacaagc   3300
tagaaaaagg agattcaatg gtgagataaa agcatgtgga atacatgatc tactgcgtga   3360
gttctgtttg atagaagctg aaataacgaa gcatatgcat gttgagagaa cttacccaac   3420
tcttccaaca caaaagaata atgttcgtcg cttcagtttt caaacaaaat tttattcagt   3480
tgatgattgt aataagctat taccacctgt tgccagatct atctacttct tttctcagtt   3540
ggatctacct gttgtaccct ataagaggta tctcaggtgt tgtttgccca tccaccgtga   3600
```

```
tgatcgtata atacatgatt tttactctcg tttcaacctt ctcagggtat tggtcatctc   3660
caagacaaat gaatacttcg agtcatttcc acttgtgatt acaaagttgt ttcatttgag   3720
atatctccaa gttcgatttc ttggagacat tcctgaatca atctcaaacc ttcaaaattt   3780
gcaaactcta atttgtagtg gtggtacttt acctgggaag atatggatga tgaagaactt   3840
gaggtatata agtataatag gcaacaaagt cacttattta ccaagtccta gaacagaaag   3900
tcttgtgaat ctagaggagt ttctgttct ttgttacaga agttgtacaa aagaagtcat   3960
ttctggcatt cccaatctaa agagattgac cattgatgta ctttctagca ttaacaacta   4020
ttttcccaat ggactaatag atatgtccag cttgacaaaa ctcgaagcat tcaagtgtaa   4080
taggtgttta tattcgaatt tcaatagttc tgttattcca acatcactta aggattttgt   4140
ttttccaaca tcacttaaga ggttgagttt aaactattat gctagtcatt tttttggga   4200
agaaatatca tcaactatta tcatgttgcc taatcttgaa gagctgaagc ttaaagattg   4260
tcgatccgat gaatatgatg aatggagttt gagtgataaa gacaaattca aaagcttgaa   4320
gttgttggta ctaaccgaca tttttttga tcgttgggaa gctaccagtg ataacttccc   4380
aaatctaaaa cgccttgttc tgaacaagtg cgacttagaa attccatcag attttgggga   4440
aatttgtact ttggaatcaa ttgagttaca tgattgcagc actagtgctg aggattctgc   4500
acgagagatt gaacaagaac aagaggagat gggaaataat atccttaagg tctacataca   4560
tggcagtcgc agtaagttct aaacagttat tcgattctct catctttgtt aaatcttacc   4620
tccttgaagt tatgatgatg acttcgattt tttgtcttgc ataggcagga aaatggaagc   4680
atatttcgag gaatcatcta atgccatctt ccaaatgcag aaccttttag attaatcttt   4740
tatgttctga ttgtttgtta aattcatgtt ttaggaataa acacgtttaa tacatgtttc   4800
gctctttctt tactatgtaa acagtaacta ttgatgtatt gttatatcta ttttgtgtta   4860
tgtgatagtt cgaaatgaat aatgtgttgg ggttttggtc tttttccctt cctatgtgga   4920
taaataaaag cccaattggt ctagcccact tatgcccata agcccaattt atggagcata   4980
cataagactt tctttaagtc ttattttcat atatcacaca taatttttac aagagagata   5040
agcatacata ttagagagaa aagagagaaa gtgcagattt tcgcacaaac cctagcagcc   5100
aatttcaaat cgcgattccc gcttcgtttc ttatctgatt aagctgattt ttggacagca   5160
cgttcctctc aacttaatct ttgattgaga actgacagag gtcgatttgg agtcccgtag   5220
ctccagattt ttgctcgtga acagcagctg ctatttggtg attttgctcc ttttacttct   5280
ctagttcttt ggtgctatct gtagttgttg ttgcctcgtt tttggcactt gttttggtga   5340
ccattttgga ga                                                       5352
```

<210> SEQ ID NO 2
<211> LENGTH: 887
<212> TYPE: PRT
<213> ORGANISM: Solanum americanum

<400> SEQUENCE: 2

```
Met Ala Ala Tyr Ser Ala Val Ile Ser Leu Leu Gln Thr Leu Ile Asp
1               5                   10                  15

Gln Gln Asn Ile Ser Glu Leu Phe His Gly His Thr Ala Gln Thr Leu
            20                  25                  30

Asp Ser Leu His Thr Thr Ala Glu Tyr Phe Gln His Val Leu Glu Asn
        35                  40                  45

Ile Thr Arg Phe Asp Ser Glu Lys Ile Lys Ser Leu Glu Glu Lys Ile
    50                  55                  60
```

-continued

```
Arg Val Val Val Ser Tyr Ala Glu Asp Val Val Ala Met Lys Ile Ser
65                  70                  75                  80

Gln Ile Ile Ile Gly Ser Ser Trp Thr Phe Gly Ile Leu Gln His Gln
                85                  90                  95

Asp Leu Leu Pro Leu Val Glu Lys Met Asp Thr Thr Lys Lys Gln Val
            100                 105                 110

Met Asp Ile Leu Ser His Asp Asp Asp Gln Ile Leu Glu Leu Thr Ala
        115                 120                 125

Gly Asp Ser Leu Ile Gly Thr Ser Ser Thr Thr Tyr Pro Met Leu Glu
    130                 135                 140

Asp Asp Ile Val Gln Gly Ile Asp Asp Asp Leu Glu Ile Ile Val Lys
145                 150                 155                 160

Arg Leu Thr Gly Pro Pro Arg Asp Leu Asp Val Val Thr Ile Thr Gly
                165                 170                 175

Met Gly Gly Ile Gly Lys Thr Thr Leu Ala Arg Lys Ala Tyr Asp His
            180                 185                 190

Leu Thr Ile Arg Tyr His Phe Asp Ile Leu Val Trp Ile Thr Ile Ser
        195                 200                 205

Gln Glu Phe Arg Cys Arg Asn Val Leu Leu Glu Ala Leu His Cys Ile
    210                 215                 220

Ser Lys Ser Thr Asp Ile Val Asn Thr Lys Asp Tyr Asp Lys Lys Asp
225                 230                 235                 240

Asp Asn Glu Leu Ala Asp Ile Val Gln Lys Lys Leu Lys Gly Pro Arg
                245                 250                 255

Tyr Leu Val Val Val Asp Asp Ile Trp Ser Arg Asp Val Trp Asp Ser
            260                 265                 270

Ile Arg Gly Ile Phe Pro Asn Tyr Asn Asn Gly Ser Arg Ile Leu Leu
        275                 280                 285

Thr Thr Arg Glu Asn Glu Val Ala Met Tyr Ala Asn Thr Cys Ser Pro
    290                 295                 300

His Glu Met Ser Leu Leu Ser Leu Glu Asn Gly Trp Arg Leu Leu Cys
305                 310                 315                 320

Asp Lys Val Phe Gly Pro Lys His Asp His Pro Pro Glu Leu Glu Glu
                325                 330                 335

Ile Gly Lys Glu Ile Val Glu Lys Cys Gln Gly Leu Pro Leu Thr Ile
            340                 345                 350

Ser Val Ile Ala Gly His Val Ser Lys Met Pro Arg Thr Leu Glu Cys
        355                 360                 365

Trp Lys Asp Val Ala Arg Thr Leu Ser Glu Ile Ile Ser Ser His Pro
    370                 375                 380

Asp Asn Cys Leu Gly Val Leu Gly Leu Ser Tyr His His Leu Pro Asn
385                 390                 395                 400

His Leu Lys Pro Cys Phe Leu Ser Met Ser Ser Phe Pro Glu Asp Phe
                405                 410                 415

Gln Val Glu Thr Arg Arg Leu Ile Tyr Leu Trp Ile Ala Glu Gly Phe
            420                 425                 430

Ile Arg Thr Cys Glu Asn Gly Lys Ser Leu Glu Glu Val Ala Val Asp
        435                 440                 445

Tyr Leu Glu Asp Leu Ile Ser Arg Asn Leu Ile Gln Ala Arg Lys Arg
    450                 455                 460

Arg Phe Asn Gly Glu Ile Lys Ala Cys Gly Ile His Asp Leu Leu Arg
465                 470                 475                 480
```

-continued

```
Glu Phe Cys Leu Ile Glu Ala Glu Ile Thr Lys His Met His Val Glu
                485                 490                 495

Arg Thr Tyr Pro Thr Leu Pro Thr Gln Lys Asn Asn Val Arg Arg Phe
            500                 505                 510

Ser Phe Gln Thr Lys Phe Tyr Ser Val Asp Asp Cys Asn Lys Leu Leu
        515                 520                 525

Pro Pro Val Ala Arg Ser Ile Tyr Phe Phe Ser Gln Leu Asp Leu Pro
    530                 535                 540

Val Val Pro Tyr Lys Arg Tyr Leu Arg Cys Cys Leu Pro Ile His Arg
545                 550                 555                 560

Asp Asp Arg Ile Ile His Asp Phe Tyr Ser Arg Phe Asn Leu Leu Arg
                565                 570                 575

Val Leu Val Ile Ser Lys Thr Asn Glu Tyr Phe Glu Ser Phe Pro Leu
            580                 585                 590

Val Ile Thr Lys Leu Phe His Leu Arg Tyr Leu Gln Val Arg Phe Leu
        595                 600                 605

Gly Asp Ile Pro Glu Ser Ile Ser Asn Leu Gln Asn Leu Gln Thr Leu
    610                 615                 620

Ile Cys Ser Gly Gly Thr Leu Pro Gly Lys Ile Trp Met Met Lys Asn
625                 630                 635                 640

Leu Arg Tyr Ile Ser Ile Ile Gly Asn Lys Val Thr Tyr Leu Pro Ser
                645                 650                 655

Pro Arg Thr Glu Ser Leu Val Asn Leu Glu Glu Phe Ser Val Leu Cys
            660                 665                 670

Tyr Arg Ser Cys Thr Lys Glu Val Ile Ser Gly Ile Pro Asn Leu Lys
        675                 680                 685

Arg Leu Thr Ile Asp Val Leu Ser Ser Ile Asn Asn Tyr Phe Pro Asn
    690                 695                 700

Gly Leu Ile Asp Met Ser Ser Leu Thr Lys Leu Glu Ala Phe Lys Cys
705                 710                 715                 720

Asn Arg Cys Leu Tyr Ser Asn Phe Asn Ser Ser Val Ile Pro Thr Ser
                725                 730                 735

Leu Lys Asp Phe Val Phe Pro Thr Ser Leu Lys Arg Leu Ser Leu Asn
            740                 745                 750

Tyr Tyr Ala Ser His Phe Phe Trp Glu Glu Ile Ser Ser Thr Ile Ile
        755                 760                 765

Met Leu Pro Asn Leu Glu Glu Leu Lys Leu Lys Asp Cys Arg Ser Asp
    770                 775                 780

Glu Tyr Asp Glu Trp Ser Leu Ser Asp Lys Asp Lys Phe Lys Ser Leu
785                 790                 795                 800

Lys Leu Leu Val Leu Thr Asp Ile Phe Phe Asp Arg Trp Glu Ala Thr
                805                 810                 815

Ser Asp Asn Phe Pro Asn Leu Lys Arg Leu Val Leu Asn Lys Cys Asp
            820                 825                 830

Leu Glu Ile Pro Ser Asp Phe Gly Glu Ile Cys Thr Leu Glu Ser Ile
        835                 840                 845

Glu Leu His Asp Cys Ser Thr Ser Ala Glu Asp Ser Ala Arg Glu Ile
    850                 855                 860

Glu Gln Glu Gln Glu Glu Met Gly Asn Asn Ile Leu Lys Val Tyr Ile
865                 870                 875                 880

His Gly Ser Arg Ser Lys Phe
                885
```

```
<210> SEQ ID NO 3
<211> LENGTH: 2661
<212> TYPE: DNA
<213> ORGANISM: Solanum americanum
<220> FEATURE:
<221> NAME/KEY: CDS
<222> LOCATION: (1)..(2661)

<400> SEQUENCE: 3

atg gca gct tat agt gct gta att tct ctt ctt caa aca ctt att gat       48
Met Ala Ala Tyr Ser Ala Val Ile Ser Leu Leu Gln Thr Leu Ile Asp
1               5                   10                  15

caa caa aat att tca gaa ctc ttt cat ggt cac act gcc caa acg ctc       96
Gln Gln Asn Ile Ser Glu Leu Phe His Gly His Thr Ala Gln Thr Leu
            20                  25                  30

gat tct ctt cac act aca gct gaa tat ttt caa cat gtc ctt gaa aat      144
Asp Ser Leu His Thr Thr Ala Glu Tyr Phe Gln His Val Leu Glu Asn
        35                  40                  45

att aca aga ttt gac tct gaa aag atc aaa tct ttg gag gaa aaa ata      192
Ile Thr Arg Phe Asp Ser Glu Lys Ile Lys Ser Leu Glu Glu Lys Ile
    50                  55                  60

aga gtt gtt gtt agc tat gca gaa gat gtt gtt gca atg aaa att tct      240
Arg Val Val Val Ser Tyr Ala Glu Asp Val Val Ala Met Lys Ile Ser
65                  70                  75                  80

caa atc atc ata ggc tca agc tgg aca ttt gga att tta caa cac cag      288
Gln Ile Ile Ile Gly Ser Ser Trp Thr Phe Gly Ile Leu Gln His Gln
                85                  90                  95

gat tta cta cca ctt gtt gaa aaa atg gac aca aca aag aaa caa gtg      336
Asp Leu Leu Pro Leu Val Glu Lys Met Asp Thr Thr Lys Lys Gln Val
            100                 105                 110

atg gac att ctt tct cat gat gat gat caa att ctt gaa tta act gca      384
Met Asp Ile Leu Ser His Asp Asp Asp Gln Ile Leu Glu Leu Thr Ala
        115                 120                 125

ggg gat tcc ttg att ggc act tct tct aca act tat cca atg ttg gaa      432
Gly Asp Ser Leu Ile Gly Thr Ser Ser Thr Thr Tyr Pro Met Leu Glu
    130                 135                 140

gat gat atc gtg cag gga att gat gat gac ttg gag atc ata gtt aaa      480
Asp Asp Ile Val Gln Gly Ile Asp Asp Asp Leu Glu Ile Ile Val Lys
145                 150                 155                 160

aga ttg aca gga cca cca cgg gat tta gac gtt gtc aca ata aca ggt      528
Arg Leu Thr Gly Pro Pro Arg Asp Leu Asp Val Val Thr Ile Thr Gly
                165                 170                 175

atg ggt ggc att ggt aaa aca aca ctc gct aga aag gct tat gat cat      576
Met Gly Gly Ile Gly Lys Thr Thr Leu Ala Arg Lys Ala Tyr Asp His
            180                 185                 190

ctc aca atc agg tat cac ttt gac att ctt gtt tgg att aca ata tct      624
Leu Thr Ile Arg Tyr His Phe Asp Ile Leu Val Trp Ile Thr Ile Ser
        195                 200                 205

caa gaa ttt cga tgt aga aat gta ttg tta gaa gct tta cat tgc att      672
Gln Glu Phe Arg Cys Arg Asn Val Leu Leu Glu Ala Leu His Cys Ile
    210                 215                 220

tca aag tca aca gat att gtg aac aca aaa gat tat gat aag aag gat      720
Ser Lys Ser Thr Asp Ile Val Asn Thr Lys Asp Tyr Asp Lys Lys Asp
225                 230                 235                 240

gac aat gag tta gct gac ata gta cag aaa aaa cta aag ggt cca aga      768
Asp Asn Glu Leu Ala Asp Ile Val Gln Lys Lys Leu Lys Gly Pro Arg
                245                 250                 255

tac cta gtt gtt gtt gat gat att tgg agt aga gat gtt tgg gat agt      816
Tyr Leu Val Val Val Asp Asp Ile Trp Ser Arg Asp Val Trp Asp Ser
            260                 265                 270

ata aga gga ata ttt cct aat tac aac aac ggg agt cga atc tta ttg      864
```

-continued

```
Ile Arg Gly Ile Phe Pro Asn Tyr Asn Asn Gly Ser Arg Ile Leu Leu
        275                 280                 285

act act agg gaa aac gag gta gca atg tat gca aat act tgt agc cct      912
Thr Thr Arg Glu Asn Glu Val Ala Met Tyr Ala Asn Thr Cys Ser Pro
    290                 295                 300

cat gag atg agt ctt ttg agt tta gaa aac ggt tgg agg tta ctt tgt      960
His Glu Met Ser Leu Leu Ser Leu Glu Asn Gly Trp Arg Leu Leu Cys
305                 310                 315                 320

gat aag gtg ttt gga cca aaa cat gat cat cct cct gaa ttg gaa gaa     1008
Asp Lys Val Phe Gly Pro Lys His Asp His Pro Pro Glu Leu Glu Glu
                325                 330                 335

att ggt aag gaa ata gtt gaa aaa tgc caa gga cta ccc tta aca att     1056
Ile Gly Lys Glu Ile Val Glu Lys Cys Gln Gly Leu Pro Leu Thr Ile
            340                 345                 350

tca gtg att gcg gga cat gtt tct aaa atg ccc agg aca tta gaa tgt     1104
Ser Val Ile Ala Gly His Val Ser Lys Met Pro Arg Thr Leu Glu Cys
        355                 360                 365

tgg aag gat gtc gcc cga acc tta agt gaa atc atc tct agt cat cca     1152
Trp Lys Asp Val Ala Arg Thr Leu Ser Glu Ile Ile Ser Ser His Pro
    370                 375                 380

gat aat tgc tta gga gtg ctc ggt ttg agt tac cat cac ttg cct aat     1200
Asp Asn Cys Leu Gly Val Leu Gly Leu Ser Tyr His His Leu Pro Asn
385                 390                 395                 400

cac ctc aaa cct tgc ttt ctt tct atg agt agt ttc cca gaa gat ttt     1248
His Leu Lys Pro Cys Phe Leu Ser Met Ser Ser Phe Pro Glu Asp Phe
                405                 410                 415

cag gtt gaa act cgg aga ttg atc tac tta tgg atc gca gaa ggt ttc     1296
Gln Val Glu Thr Arg Arg Leu Ile Tyr Leu Trp Ile Ala Glu Gly Phe
            420                 425                 430

ata agg act tgc gaa aat ggt aaa agt ttg gag gaa gtt gca gta gat     1344
Ile Arg Thr Cys Glu Asn Gly Lys Ser Leu Glu Glu Val Ala Val Asp
        435                 440                 445

tat ttg gag gac ctt att agc agg aac ttg ata caa gct aga aaa agg     1392
Tyr Leu Glu Asp Leu Ile Ser Arg Asn Leu Ile Gln Ala Arg Lys Arg
    450                 455                 460

aga ttc aat ggt gag ata aaa gca tgt gga ata cat gat cta ctg cgt     1440
Arg Phe Asn Gly Glu Ile Lys Ala Cys Gly Ile His Asp Leu Leu Arg
465                 470                 475                 480

gag ttc tgt ttg ata gaa gct gaa ata acg aag cat atg cat gtt gag     1488
Glu Phe Cys Leu Ile Glu Ala Glu Ile Thr Lys His Met His Val Glu
                485                 490                 495

aga act tac cca act ctt cca aca caa aag aat aat gtt cgt cgc ttc     1536
Arg Thr Tyr Pro Thr Leu Pro Thr Gln Lys Asn Asn Val Arg Arg Phe
            500                 505                 510

agt ttt caa aca aaa ttt tat tca gtt gat gat tgt aat aag cta tta     1584
Ser Phe Gln Thr Lys Phe Tyr Ser Val Asp Asp Cys Asn Lys Leu Leu
        515                 520                 525

cca cct gtt gcc aga tct atc tac ttc ttt tct cag ttg gat cta cct     1632
Pro Pro Val Ala Arg Ser Ile Tyr Phe Phe Ser Gln Leu Asp Leu Pro
    530                 535                 540

gtt gta ccc tat aag agg tat ctc agg tgt tgt ttg ccc atc cac cgt     1680
Val Val Pro Tyr Lys Arg Tyr Leu Arg Cys Cys Leu Pro Ile His Arg
545                 550                 555                 560

gat gat cgt ata ata cat gat ttt tac tct cgt ttc aac ctt ctc agg     1728
Asp Asp Arg Ile Ile His Asp Phe Tyr Ser Arg Phe Asn Leu Leu Arg
                565                 570                 575

gta ttg gtc atc tcc aag aca aat gaa tac ttc gag tca ttt cca ctt     1776
Val Leu Val Ile Ser Lys Thr Asn Glu Tyr Phe Glu Ser Phe Pro Leu
            580                 585                 590
```

-continued

```
gtg att aca aag ttg ttt cat ttg aga tat ctc caa gtt cga ttt ctt     1824
Val Ile Thr Lys Leu Phe His Leu Arg Tyr Leu Gln Val Arg Phe Leu
        595                 600                 605

gga gac att cct gaa tca atc tca aac ctt caa aat ttg caa act cta     1872
Gly Asp Ile Pro Glu Ser Ile Ser Asn Leu Gln Asn Leu Gln Thr Leu
    610                 615                 620

att tgt agt ggt ggt act tta cct ggg aag ata tgg atg atg aag aac     1920
Ile Cys Ser Gly Gly Thr Leu Pro Gly Lys Ile Trp Met Met Lys Asn
625                 630                 635                 640

ttg agg tat ata agt ata ata ggc aac aaa gtc act tat tta cca agt     1968
Leu Arg Tyr Ile Ser Ile Ile Gly Asn Lys Val Thr Tyr Leu Pro Ser
                645                 650                 655

cct aga aca gaa agt ctt gtg aat cta gag gag ttt tct gtt ctt tgt     2016
Pro Arg Thr Glu Ser Leu Val Asn Leu Glu Glu Phe Ser Val Leu Cys
            660                 665                 670

tac aga agt tgt aca aaa gaa gtc att tct ggc att ccc aat cta aag     2064
Tyr Arg Ser Cys Thr Lys Glu Val Ile Ser Gly Ile Pro Asn Leu Lys
        675                 680                 685

aga ttg acc att gat gta ctt tct agc att aac aac tat ttt ccc aat     2112
Arg Leu Thr Ile Asp Val Leu Ser Ser Ile Asn Asn Tyr Phe Pro Asn
    690                 695                 700

gga cta ata gat atg tcc agc ttg aca aaa ctc gaa gca ttc aag tgt     2160
Gly Leu Ile Asp Met Ser Ser Leu Thr Lys Leu Glu Ala Phe Lys Cys
705                 710                 715                 720

aat agg tgt tta tat tcg aat ttc aat agt tct gtt att cca aca tca     2208
Asn Arg Cys Leu Tyr Ser Asn Phe Asn Ser Ser Val Ile Pro Thr Ser
                725                 730                 735

ctt aag gat ttt gtt ttt cca aca tca ctt aag agg ttg agt tta aac     2256
Leu Lys Asp Phe Val Phe Pro Thr Ser Leu Lys Arg Leu Ser Leu Asn
            740                 745                 750

tat tat gct agt cat ttt ttt tgg gaa gaa ata tca tca act att atc     2304
Tyr Tyr Ala Ser His Phe Phe Trp Glu Glu Ile Ser Ser Thr Ile Ile
        755                 760                 765

atg ttg cct aat ctt gaa gag ctg aag ctt aaa gat tgt cga tcc gat     2352
Met Leu Pro Asn Leu Glu Glu Leu Lys Leu Lys Asp Cys Arg Ser Asp
    770                 775                 780

gaa tat gat gaa tgg agt ttg agt gat aaa gac aaa ttc aaa agc ttg     2400
Glu Tyr Asp Glu Trp Ser Leu Ser Asp Lys Asp Lys Phe Lys Ser Leu
785                 790                 795                 800

aag ttg ttg gta cta acc gac att ttt ttt gat cgt tgg gaa gct acc     2448
Lys Leu Leu Val Leu Thr Asp Ile Phe Phe Asp Arg Trp Glu Ala Thr
                805                 810                 815

agt gat aac ttc cca aat cta aaa cgc ctt gtt ctg aac aag tgc gac     2496
Ser Asp Asn Phe Pro Asn Leu Lys Arg Leu Val Leu Asn Lys Cys Asp
            820                 825                 830

tta gaa att cca tca gat ttt ggg gaa att tgt act ttg gaa tca att     2544
Leu Glu Ile Pro Ser Asp Phe Gly Glu Ile Cys Thr Leu Glu Ser Ile
        835                 840                 845

gag tta cat gat tgc agc act agt gct gag gat tct gca cga gag att     2592
Glu Leu His Asp Cys Ser Thr Ser Ala Glu Asp Ser Ala Arg Glu Ile
    850                 855                 860

gaa caa gaa caa gag gag atg gga aat aat atc ctt aag gtc tac ata     2640
Glu Gln Glu Gln Glu Glu Met Gly Asn Asn Ile Leu Lys Val Tyr Ile
865                 870                 875                 880

cat ggc agt cgc agt aag ttc                                         2661
His Gly Ser Arg Ser Lys Phe
                885
```

LATE BLIGHT RESISTANCE GENE FROM *SOLANUM AMERICANUM* AND METHODS OF USE

CROSS-REFERENCE TO RELATED APPLICATIONS

This application is the U.S. National Stage of International Application PCT/US2016/031119, filed May 6, 2016, which designates the U.S and was published by the International Bureau in English on Nov. 17, 2016, and which claims the benefit of U.S. Provisional Patent Application No. 62/159,240, filed May 9, 2015, all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0095.TXT, created on Apr. 22, 2016, and having a size of 27.4 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Late blight, caused by oomycete pathogen *Phytophthora infestans,* is a devastating disease of cultivated potato (*Solanum tuberosum*) and tomato (*Solanum lycopersicum*), causing several billion dollars annual losses (Jones (2014) *Philos. Trans. R. Soc. Lond. B Biol. Sci.* 369:20130087-20130087). It was estimated that only in Europe late blight cost in potato production is over 1 billion euros including costs of control and damage caused by the pathogen (Haverkort (2008) *Potato Res.* 51:47-57).

Plant breeders have typically introduced one Rpi (i.e. Resistance to *Phytophthora infestans*) gene at a time from wild relatives into cultivated potato. However, this process is laborious and slow, and so far has resulted in an Rpi gene that is overcome by new *P. infestans* races in less time than it took to breed the new potato variety that contains it (Jones et al. 2014). A transgenic approach allows introduction of several genes at the same time ('gene stacking'), providing more durable resistance. Several major genes conferring resistance against late blight has been reported, however due to quick *P. infestans* evolution, there is still need to clone additional Rpi genes.

Cloned Rpi genes and their functional alleles include, for example: Rpi-blb1/RB from *Solanum demissum* (van der Vossen et al. (2003) *Plant J.* 36:867-882; Song et al. (2003) *PNAS* 100:9128-9133) and its homologues Rpi-sto1 and Rpi-pta1 from *S. stoloniferum* and *S. papita,* respectively (Vleeshouwers et al. (2008) *PLOS ONE* 3:e2875); Rpi-blb2 from *S. demissum* (van der Vossen EA et al. (2005) *Plant J.* 44:208-222); Rpi-blb3 and its homologues Rpi-abpt and R2-like from *S. bulbocastanum* and R2 from *S. demissum* (Lokossou et al. (2009) *MPMI* 22:630-641) and additional homologues Rpi-edn1.1, Rpi-edn1.2, Rpi-snk1.1, Rpi-snk1.2 and Rpi-hjt1.1-Rpi-hjt1.3 from *S. edinense, S. schenckii* and *S. hjertingii,* respectively, described by Champouret ((2010) "Functional genomics of *Phytophthora infestans* effectors and *Solanum* resistance genes," PhD Thesis, Wageningen Univ., Wageningen); Rpi-bt1 from *S. demissum* (Oosumi et al. (2009) *Amer. J. Potato Res.* 86:456-465); R1 from *S. demissum* (Ballvora et al. (2002) *Plant J.* 30:361-71); R3a and R3b from *S. demissum* (Huang et al. (2005) *Plant J.* 42:261-271; Li et al. (2011) *MPMI* 24:1132-1142; respectively); Rpi-vnt1.1, Rpi-vnt1.2, Rpi-vnt1.3 from *S. venturii* (Foster et al. (2009) *MPMI* 22:589-600; Pel et al. (2009) *MPMI* 22:601-615; WO2009013468); Rpi-mcq1 from *S. mochiquense* (WO2009013468); Rpi-chc from *S. chacoense* (WO2011034433) and Ph-3 from *S. pimpinellifolium* (Zhang et al. (2014) *Theor. Appl. Genet.* 127:1353-1364).

*Solanum nigrum* and closely related species are generally regarded as non-hosts for infection by *P. infestans.* They are not infected under laboratory conditions, and infections are very rarely observed in the field (Lebecka (2009) *Eur. J. Plant Pathol.*124:345-348). However, there is one report of *S. nigrum* susceptibility to *P. infestans* infection, and of Mendelian segregation for resistance when a susceptible line is crossed to a resistant line, and the F1 selfed to produce F2 progeny (Lebecka (2008) *Eur. J. Plant Pathol.* 120:233-240; Lebecka (2009) *Eur. J. Plant Pathol.* 124:345-348). This resistance under strong pathogen pressure suggests that resistance genes present in *S. nigrum* might have unique efficacy and recognition specificities, making them valuable to clone and characterize. *S. nigrum* is a hexaploid plant of complex polyploid origin, making classical map-based cloning laborious and time consuming. To overcome these limitations, we have explored the resistance and susceptibility to *P. infestans* in accessions of *S. americanum,* a putative diploid ancestor of *S. nigrum* (Poczai and Hyvonen (2010) *Mol. Biol. Rep.* 38:1171-1185). *S. americanum* is herbaceous flowering plant growing worldwide, originating probably from subtropics of the Americas.

While traditional map-based cloning methods have been employed to isolate resistance (R) genes from plants, many plant genomes carry large chromosomal regions that are inaccessible to traditional map-based cloning due to suppressed recombination (Gaut et al. (2007) *Nature Rev. Genet.* 8:77-84) and solanaceous plants are no exception. Therefore, new approaches not relying on recombination need to be applied to rapidly identify additional Rpi genes from cultivated solanaceous plants and their undomesticated relatives in the Solanaceae family.

BRIEF SUMMARY OF THE INVENTION

The present invention provides nucleic acid molecules for resistance (R) genes that are capable of conferring to a plant, particularly a solanaceous plant, resistance to at least one race of a *Phytophthora* species (sp.) that is known to cause a plant disease in the plant. In one embodiment, the present invention provides nucleic acid molecules comprising an R gene, which is referred to herein as Rpi-amr3i, and its variants including, for example, orthologs and non-naturally occurring variants.

The present invention further provides plants, plant cells, and seeds comprising in their genomes one or more polynucleotide constructs of the invention. The polynucleotide constructs comprise a nucleotide sequence encoding a resistance (R) protein of the present invention. Such R proteins are encoded by the R genes of the present invention. In a preferred embodiment, the plants and seeds are transgenic solanaceous plants and seeds that have been transformed with one or more polynucleotide constructs of the invention. Preferably, such solanaceous plants comprise enhanced resistance to at least one race of a *Phytophthora* sp. that is known to cause a plant disease in a solanaceous plant, when compared to the resistance of a control plant that does not comprise the polynucleotide construct. Solanaceous plants of the invention include, but are not limited to, domesticated solanaceous plants including, for example, domesticated varieties of potato and tomato.

The present invention provides methods for enhancing the resistance of a plant, particularly a solanaceous plant, to a plant disease caused by at least one race of at least one *Phytophthora* sp. Such methods comprise introducing into at least one plant cell a polynucleotide construct comprising a nucleotide sequence of an R gene of the present invention. Preferably, the polynucleotide construct or part thereof is stably incorporated into the genome of the plant cell. The methods can optionally further comprise regenerating the plant cell into a plant that comprises in its genome the polynucleotide construct. Preferably, such a plant comprises enhanced resistance to a plant disease caused by at least one race of a *Phytophthora* sp., relative to a control plant not comprising the polynucleotide construct. More preferably, such a plant comprises enhanced resistance to plant disease(s) caused by at least two, three, four, five, or more races of a *Phytophthora* sp., relative to a control plant not comprising the polynucleotide construct.

The present invention additionally provides methods for identifying a solanaceous plant that displays newly conferred or enhanced resistance to a plant disease caused by at least one race of a *Phytophthora* sp. The methods comprise detecting in the solanaceous plant the presence of the R gene, Rpi-amr3i.

Methods of using the plants of the present invention in agricultural crop production to limit plant disease caused by at least one race of a *Phytophthora* sp. are also provided. The methods comprise planting a plant (e.g. a seedling), a tuber, or a seed of the present invention, wherein the plant, tuber, or seed comprises at least one R gene nucleotide sequence of the present invention. The methods further comprise growing a plant under conditions favorable for the growth and development of the plant, and optionally harvesting at least one fruit, tuber, leaf, or seed from the plant.

Additionally provided are plants, plant parts, seeds, plant cells, other host cells, expression cassettes, and vectors comprising one or more of the nucleic acid molecules of the present invention.

FIG. 1 is a photographic illustration showing the phenotypes of various *Solanum americanum* lines infected with *P. infestans* in detached leaf assay. Ten-week-old *S. americanum* plants were infected with race 88069 of *P. infestans*. Top to bottom: only accession 954750186 was susceptible to all tested races, while accessions 954750174, 954750184 and 944750095 remained fully resistant. Each leaf was inoculated with 6-8 droplets containing 1,000 spores; photographs were taken 7 days post inoculation (dpi).

Figure 2:
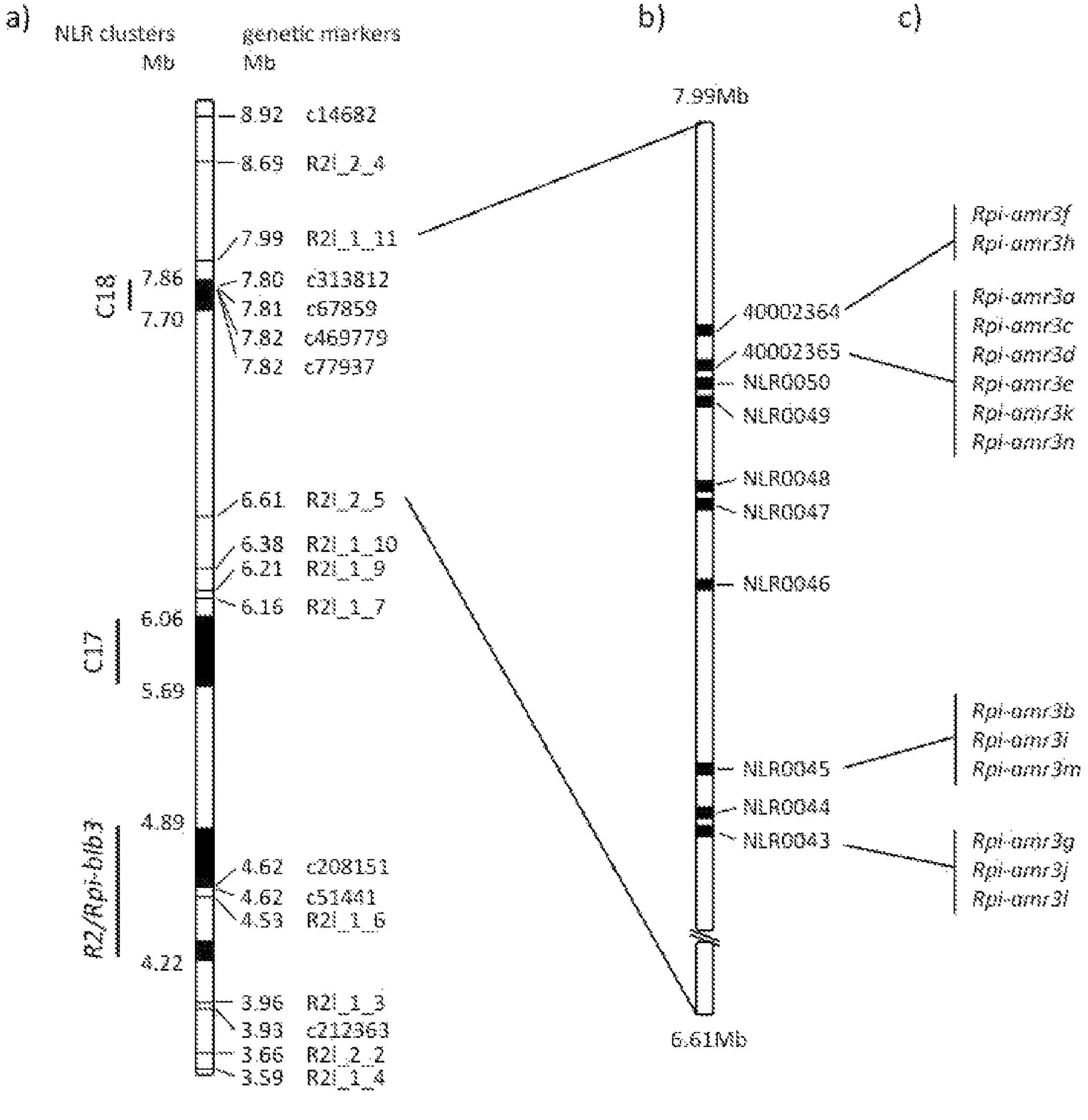

FIG. 2 is a physical linkage map of loci R2/Rpi-blb3, C17 and C18 based on DM reference genome. Part a): Bulked Segregant Analysis (BSA) coupled with RenSeq enables positioning of Rpi-amr3 on an approximately 5.1 Mb (3.6-8.7 Mb) interval on Ch4. Genotyping of 50 susceptible F2 and F3 plants with markers derived from Whole Genome Shotgun sequencing (WGS) data resulted in two flanking markers, R2l_1_4 at 3.59 Mb and R2l_2_4 at 8.69 Mb, and an additional eight "co-segregating with resistance" (R2l markers). Physical positions of NLR genes and markers are given in Mb, and are based on the reference doubled monohaploid (DM) potato genome. Markers beginning with 'c' are RenSeq markers, and with 'R2l' are WGS markers. Black solid bars mark NLR clusters. Part b): Genotyping and phenotyping of 405 plants from backcross population ($BC_1F_2$) confirmed location of Rpi-amr at the C18 locus (10 NLRs in reference DM genome), between markers R2l_2_5 at 6.61 Mb and R2l_1_11 at 7.99 Mb on a physical map of DM. Part c): Alignment of PacBio-RenSeq derived de novo assembly to C18 DM locus resulted in 14 full length C18 paralog Rpi-amr3 candidates.

Figure 3:
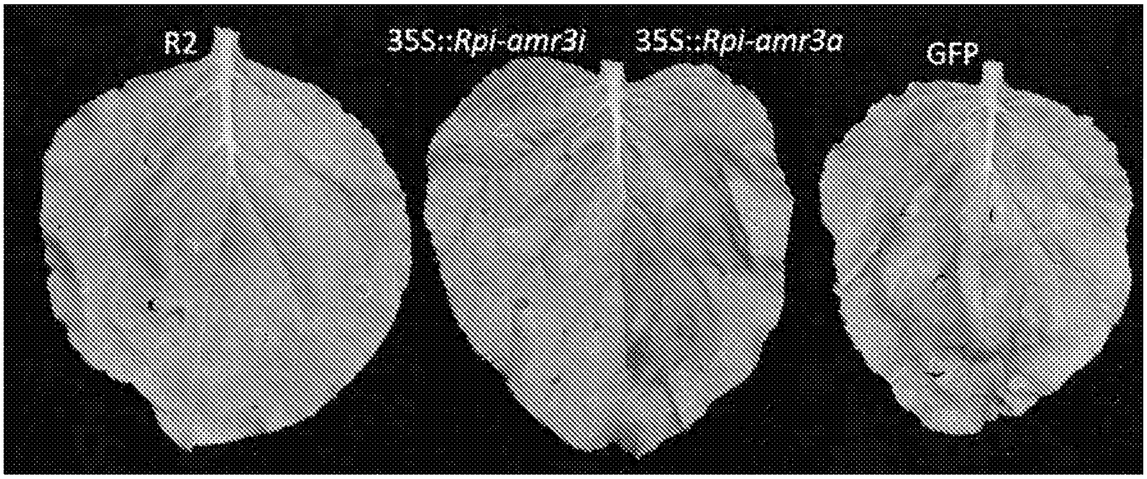

FIG. 3. is a photographic illustration showing that the candidate Rpi-amr3i confers resistance against *P. infestans* in a transient complementation assay in *N. benthamiana* leaves. Third leaves of *N. benthamiana* plants were infiltrated with the vector pICSLUS0003:35S overexpressing R2 (positive control), Rpi-amr3 candidates or GFP (negative control), and 24 hours later inoculated with the *P. infestans* race 88069. No *P. infestans* growth was observed for R2 and Rpi-amr3i (pictured), while *P. infestans* growth was unaltered at infiltration sites of all other Rpi-amr3 candidates and the GFP control. The figure shows Rpi-amr3a as an example of the phenotype observed for all other candidate genes. The photographs were taken 6 dpi.

Figure 4:
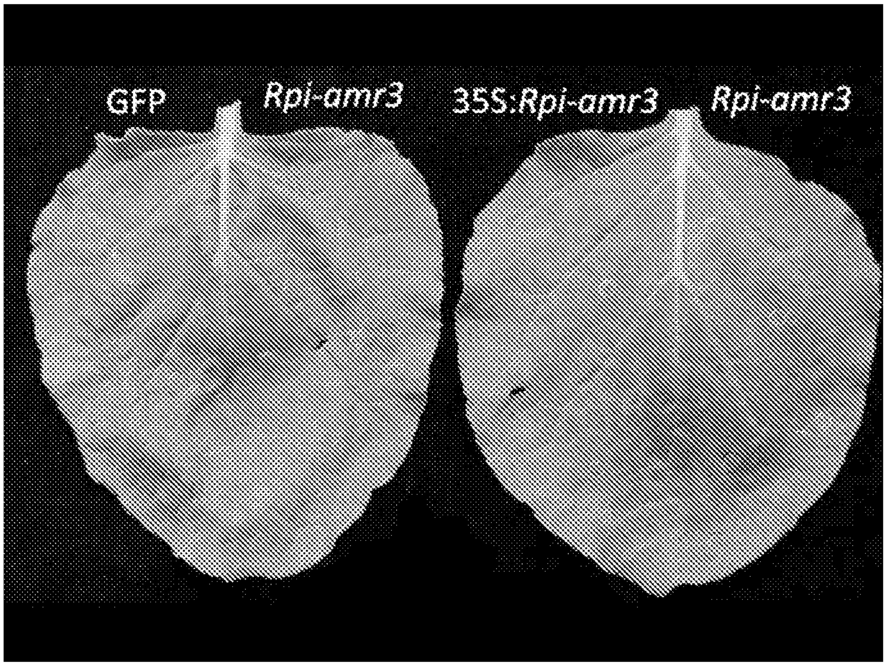

FIG. 4 is a photographic illustration showing that a genomic construct with Rpi-amr3i confers resistance against *P. infestans* in transient complementation assay in *N. benthamiana* leaves. In transient complementation assay with the Rpi-amr3 genomic construct (native promoter and terminator), Rpi-amr3 restricts growth of *P. infestans* to the same level as under the 35S promoter. A vector overexpressing GFP was used as a negative control. The experiment was performed as described previously. The photographs were taken after 6 dpi.

Figure 5:
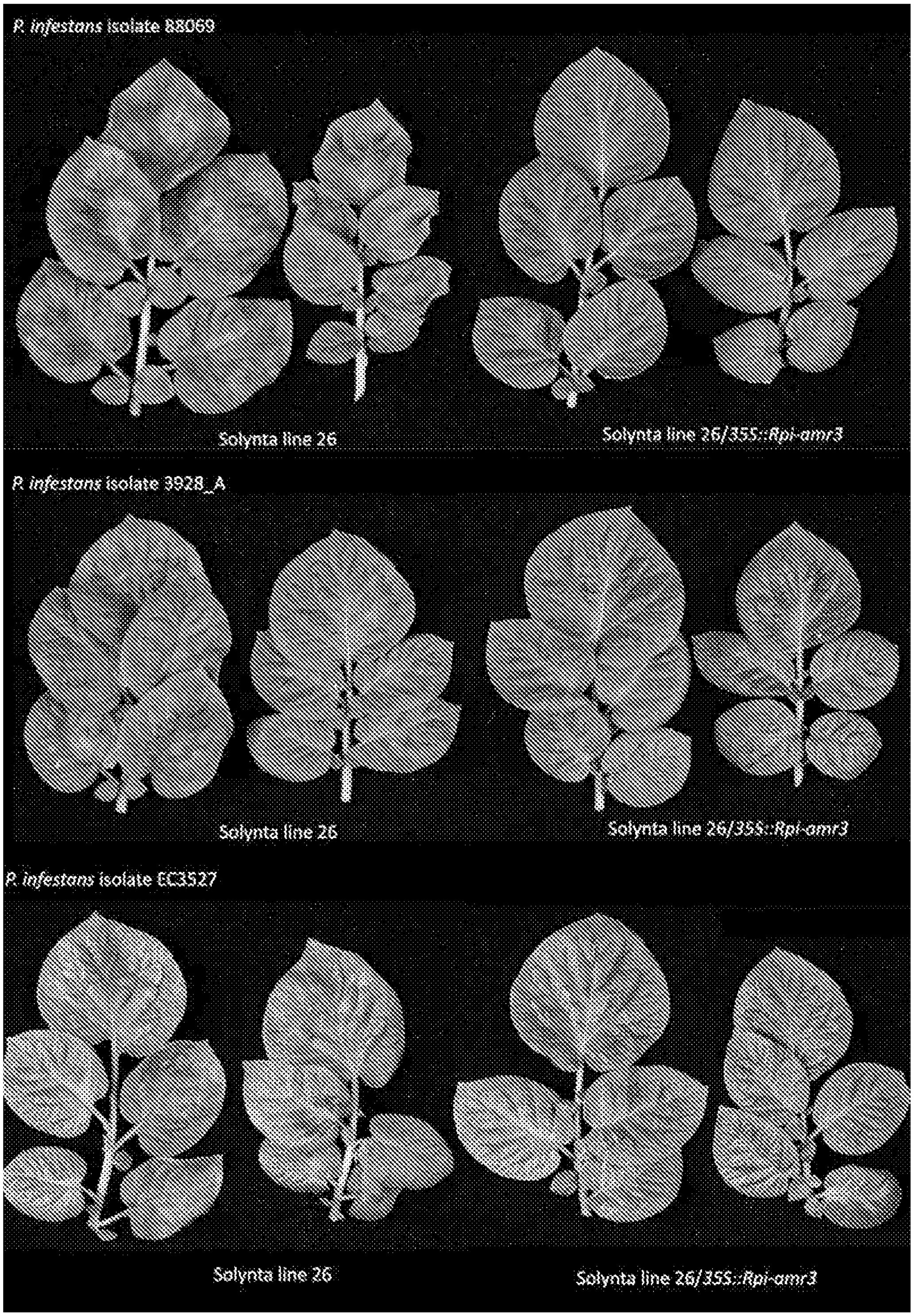

FIG. 5 is a photographic illustration of leaves of stable transgenic potato plants carrying Rpi-amr3 under the control of the 35S promoter demonstrating resistance to various *P. infestans* races. Transformants of the diploid potato Line 26 (kindly make available by Pim Lindhout, Solynta) expressing 35S:Rpi-amr3 are resistant to *P. infestans* races 88069 (upper right), 3926_A (middle right) and EC3527 (lower right). The transgenic line displays no symptoms or a weak HR at the place of inoculation. The non-transgenic control (left) showed large necrotic lesions and sporulation. Each leaf was inoculated with a droplet containing 1,000 spores; photographs were taken 6 dpi.

Figure 6:
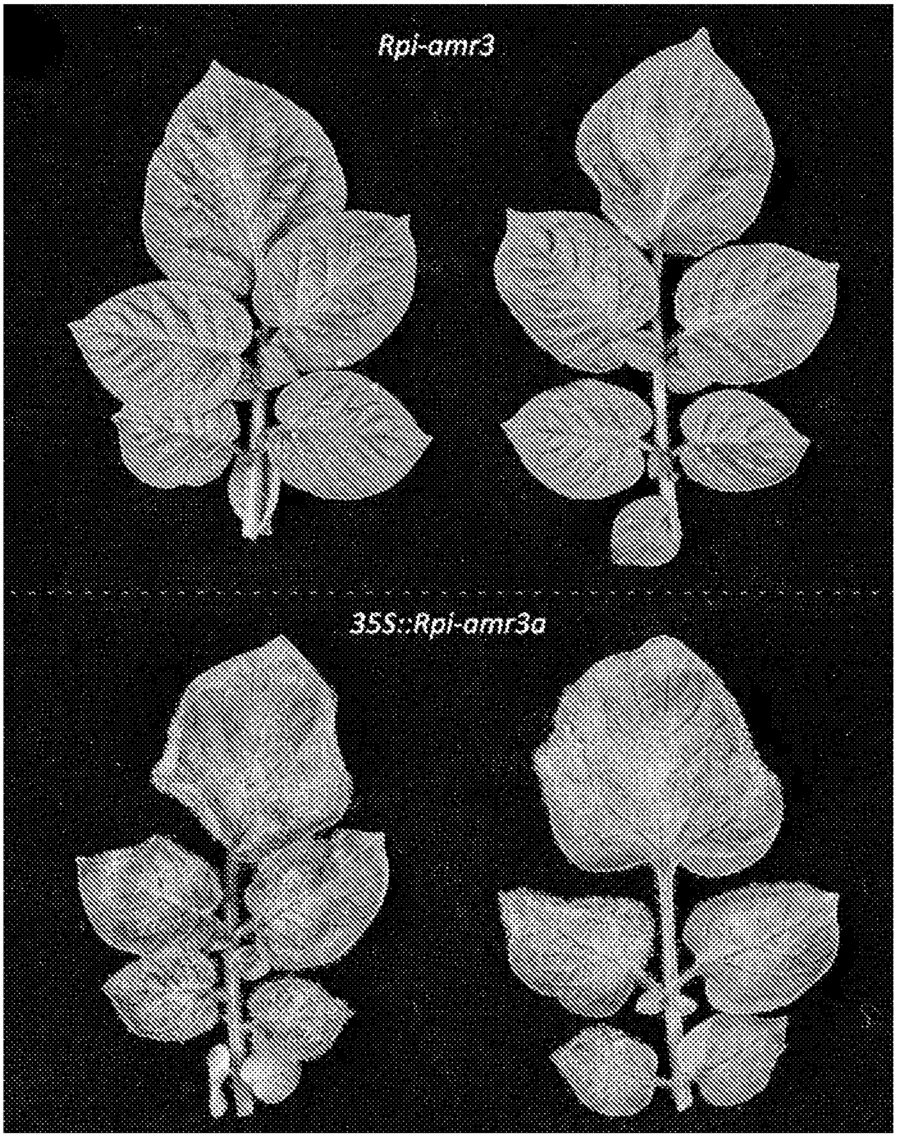

FIG. 6 is a photographic illustration of leaves of stable transgenic potato plants, line Solynta 26, carrying Rpi-amr3 under the control of the native regulatory elements demonstrating resistance to *P. infestans* race 88069. Transgenic diploid potato "Line 26" (Solynta B. V.) which expresses Rpi-amr3i under the native regulatory elements is resistant to *P. infestans* isolates 88069 (top). The transgenic line displays no to weak HR at the spot of inoculation. In contrast, the control plants carrying non-functional candidate (Rpi-amr3a, bottom) show large necrotic lesions and sporulation. Each leaflet was inoculated with a droplet containing 500 zoospores; photographs were taken 6 dpi.

Figure 7:
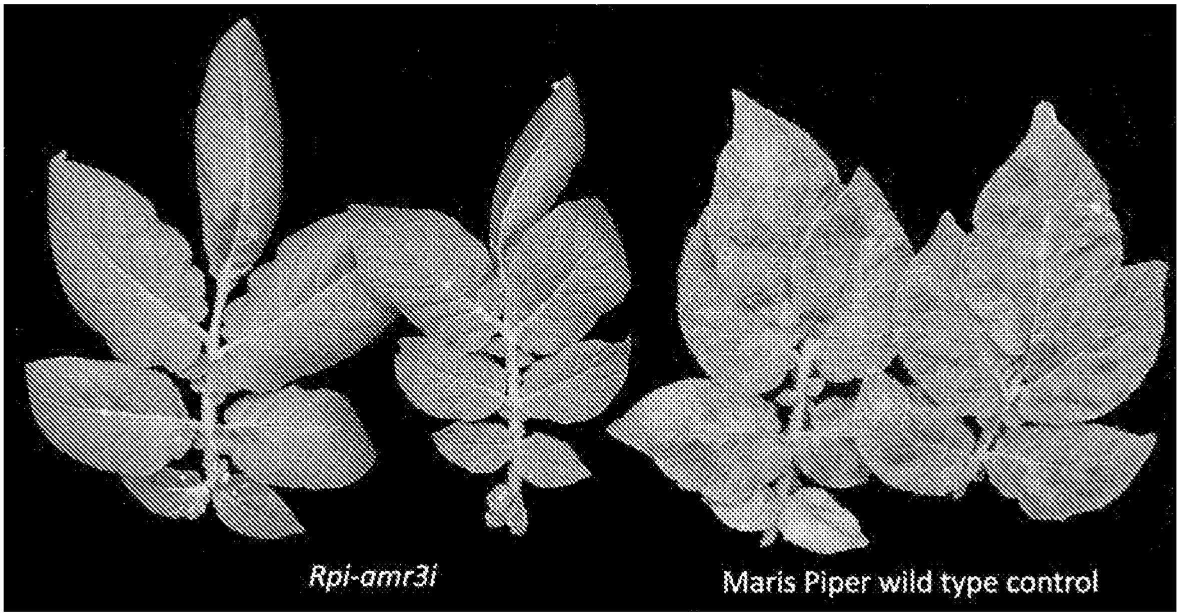

FIG. 7 is a photographic illustration of leaves of stable transgenic potato plants, cultivar Maris Piper, carrying Rpi-amr3 under the control of the native regulatory elements demonstrating resistance to various *P. infestans* races. Transgenic tetraploid potato Maris Piper which expresses Rpi-amr3i under the native regulatory elements is resistant to *P. infestans* isolates 88069 (left). The transgenic line displays no to weak HR at the spot of inoculation. In contrast, the control wild type Maris Piper plants show large necrotic lesions and sporulation. Each leaflet was inoculated with a droplet containing 500 zoospores; photographs were taken 6dpi.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the R gene, Rpi-amr3i.

SEQ ID NO: 2 sets forth the amino acid sequence of Rpi-amr3i, the R protein encoded by Rpi-amr3i.

SEQ ID NO: 3 sets forth the nucleotide sequence of the coding region of the Rpi-amr3i cDNA. If desired, a stop codon (e.g. TAA, TAG, TGA) can be operably linked to the 3' end of nucleic acid molecule comprising SEQ ID NO: 3.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to the isolation of a plant resistance (R) gene, particularly an R gene that confers upon a solanaceous plant resistance to late blight disease caused by multiple races of *Phytophthora infestans*. As disclosed hereinbelow, the R gene, referred to herein as Rpi-amr3i, was isolated from *Solanum americanum*, a diploid, non-tuber-bearing relative of potato. Rpi-amr3i was isolated from *S. americanum* using a method involving R gene sequence capture (RenSeq) with long read sequencing that has been previously described (Eid et al. (2008) *Science* 323:133-138; Sharon et al. (2013) *Nat. Biotechnol.* 31:1009-14; both of which are herein incorporated by reference).

The present invention provides nucleic acid molecules comprising the nucleotide sequences of R genes, particularly the nucleotide sequence of Rpi-amr3i and naturally occurring (e.g. orthologs and allelic variants) and synthetic or artificial (i.e. non-naturally occurring) variants thereof. Such nucleotide sequences of R genes, which are also referred to herein as R gene nucleotide sequences, encode R proteins. R gene nucleotide sequences of the invention include, but not limited to, wild-type R genes comprising a native promoter and the 3' adjacent region comprising the coding region, cDNA sequences, and nucleotide sequences comprising only the coding region. Examples of such R gene nucleotide sequences include the nucleotide sequences set forth in SEQ ID NO: 1 and SEQ NO: 3 and variants thereof. In embodiments in which the native R gene promoter is not used to drive the expression of the nucleotide sequence encoding the R protein, a heterologous promoter can be operably linked a nucleotide sequence encoding an R protein of the invention to drive the expression of nucleotide sequence encoding an R protein in a plant.

Preferably, the R proteins of the invention are functional R proteins that are capable of conferring on a plant, particularly a solanaceous plant, comprising the R protein enhanced resistance to a plant disease caused by at least one race of at least one *Phytophtora* sp. In certain preferred embodiments, the R proteins of the present invention comprise broad-spectrum resistance to multiple races of *Phytophthora infestans* such as, for example, Rpi-amr3i, the R protein encoded by Rpi-amr3i.

The present invention further provides transgenic plants comprising a polynucleotide construct which comprises an R gene nucleotide sequence of the invention. In some embodiments, the polynucleotide construct is stably incorporated into the genome of the plant, and in other embodiments, the plant is transformed by a transient transformation method and the polynucleotide construct is not stably incorporated into the genome of the plant. Methods for both the stable and transient transformation of plants are disclosed elsewhere herein or otherwise known in the art. In a preferred embodiment of the invention, the transgenic plants are stably transformed potato or tomato plants that comprise enhanced resistance to late blight disease caused by at least one race of *P. infestans*. In a more preferred embodiment of the invention, the transgenic plants are stably transformed potato or tomato plants that comprise enhanced resistance to late blight disease caused by at least two, three, four, five, six or more races of *P. infestans*.

In certain embodiments, a transgenic plant of the invention comprises a polynucleotide construct comprising a nucleotide sequence encoding an R protein and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

In certain embodiments of the invention, the transgenic plant, particularly a transgenic solanaceous plant, can comprise one, two, three, four, five, six, or more nucleotide sequences encoding an R protein. Typically, but not necessarily, the two or more R proteins will be different from each other. For the present invention, an R protein is different from another R protein when the two R proteins have non-identical amino acid sequences. In certain embodiments of the invention, each of the different R proteins for resistance to a plant disease caused by a *Phytophtora* sp. has one or more differences in resistance characteristics such as, for example, resistance against a different race and/or group of races of the same *Phytophtora* sp. or even a different *Phytophtora* sp. It is recognized that by combining two, three, four, five, six, or more nucleotide sequences with each nucleotide sequence encoding a different R protein for resistance to a different race of a *Phytophtora* sp. or *Phytophtora* species (spp.), a solanaceous plant can be produced that comprises broad spectrum resistance against multiple races of a single *Phytophtora* sp. or even multiple *Phytophtora* spp. Such a solanceous plant, particularly a potato or tomato plant, finds use in agriculture in regions where multiple races of a *Phytophtora* sp., such as, for example, multiple races of *P. infestans,* are prevalent.

Examples of R genes that can be combined in single potato plant with an Rpi-amr3i nucleotide sequence of the present invention include, but are not limited to, the following cloned Rpi genes: Rpi-blb1 (also known as "RB"; Accession Nos. FB764493.1 and AY336128.1), Rpi-sto1 (Accession No. EU884421), Rpi-pta1 (Accession No. EU884422), Rpi-blb2 (Accession No. DQ122125), Rpi-blb3 (Accession No. FJ536326), Rpi-abpt (Accession No. FJ536324), R2-like (Accession No. FJ536323), R2 (Accession No. FJ536325), Rpi-edn1.1 (Accession No. GU563963), Rpi-edn1.2, Rpi-snk1.1, Rpi-snk1.2, Rpi-hjt1.1 Rpi-hjt1.3 (Accession No. GU563971-3), Rpi-bt1 (Accession No. FJ188415), R1 (Accession No. AF447489), R3a (Accession No. AY849382), R3b (Accession No. JF900492), Rpi-vnt1.1 (Accession No. FJ423044), Rpi-vnt1.2 (Accession No. FJ423045), Rpi-vnt1.3 (Accession No. FJ423046), Rpi-mcq1 (Accession No. GN043561), Rpi-chc, and Ph-3 (Accession No. KJ563933). The nucleotide sequences corresponding to the accession numbers of the genes listed above or of any genes or proteins disclosed elsewhere herein can be obtained from publically accessible, online nucleotide and amino acid sequence databases such as, for example, the GenBank and EMBL databases (available on the World Wide Web at ncbi.nlm.nih.gov/genbank and ebi.ac.uk, repectively).

A transgenic plant of the invention comprising multiple R genes can be produced by transforming a plant that already comprises one or more other R gene nucleotide sequences with a polynucleotide construct comprising an R gene nucleotide sequence of the invention including, for example, an Rpi-amr3i nucleotide sequence or variant thereof. Such a plant that already comprises one or more other R gene nucleotide sequences can comprise R genes that are native to the genome or the plant, that were introduced into the plant via sexual reproduction, or that were introduced by transforming the plant or a progenitor thereof with an R gene nucleotide sequence. Alternatively, the one or more other R gene nucleotide sequences can be introduced into a transgenic plant of the invention, which already comprises a polynucleotide construct of the invention, by, for example, transformation or sexual reproduction.

In other embodiments, two or more different R gene sequences can be introduced into a plant by stably transforming the plant with a polynucleotide construct or vector comprising two or more R gene nucleotide sequences. It is recognized that such an approach can be preferred for plant breeding as it is expected that the two or more R gene nucleotide sequences will be tightly linked and thus, segregate a single locus. Alternatively, a polynucleotide construct of the present invention can be incorporated into the genome of a plant in the immediate vicinity of another R gene nucleotide sequence using homologous recombination-based genome modification methods that are described elsewhere herein or otherwise known in the art.

The present invention further provides methods for enhancing the resistance of a plant to a plant disease caused by at least one race of at least one *Phytophthora* sp. The methods comprise introducing a polynucleotide construct of the invention into at least one plant cell, particular a plant cell from a solanaceous plant. In certain embodiments, the polynucleotide construct is stably incorporated into the genome of the plant cell. If desired, the methods can further comprise regenerating the plant cell into a plant comprising in its genome the polynucleotide construct. Preferably, such a regenerated plant comprises enhanced resistance to a plant disease caused by at least one race of at least one *Phytophthora* sp., relative to the resistance of a control plant to the plant disease. If desired, the method can further comprise producing a plant, as described above, comprising one, two, three, four, five, six, or more nucleotide sequences encoding an R protein, preferably each nucleotide sequence encoding a different R protein.

The plants disclosed herein find use in methods for limiting plant disease caused by at least one race of at least one *Phytophthora* sp. in agricultural crop production, particularly in regions where such a plant disease is prevalent and is known to negatively impact, or at least has the potential to negatively impact, agricultural yield. The methods of the invention comprise planting a plant (e.g. a seedling), tuber, or seed of the present invention, wherein the plant, tuber, or seed comprises at least one R gene nucleotide sequence of the present invention. The methods further comprise growing the plant that is derived from the seedling, tuber, or seed under conditions favorable for the growth and development of the plant, and optionally harvesting at least one fruit, tuber, leaf, or seed from the plant.

The present invention additionally provides methods for identifying a solanaceous plant that displays newly conferred or enhanced resistance to a plant disease caused by at least one race of a *Phytophthora* sp. The methods find use in breeding solanaceous plants for resistance to plant diseases caused by *Phytophthora* spp. such as, for example, late blight disease. Such resistant plants find use in the agricultural production of fruits, tubers, leaves, and/or seeds for human or livestock consumption or other use. The methods comprise detecting in a solanaceous plant, or in at least one part or cell thereof, the presence of the R gene, Rpi-amr3i. In some embodiments of the invention, detecting the presence of the R gene comprises detecting the entire R gene in genomic DNA isolated from a solanaceous plant. In preferred embodiments, however, detecting the presence of an R gene comprises detecting the presence of at least one marker within the R gene. In other embodiments of the invention, detecting the presence of an R gene comprises detecting the presence of the R protein encoded by the R gene using, for example, immunological detection methods involving antibodies specific to the R protein.

In the methods for identifying a solanaceous plant that displays newly conferred or enhanced resistance to a plant disease caused by at least one race of a *Phytophthora* sp., detecting the presence of the R gene in the solanaceous plant can involve one or more of the following molecular biology techniques that are disclosed elsewhere herein or otherwise known in the art including, but not limited to, isolating genomic DNA and/or RNA from the plant, amplifying nucleic acid molecules comprising the R gene and/or marker therein by PCR amplification, sequencing nucleic acid molecules comprising the R gene and/or marker, identifying the R gene, the marker, or a transcript of the R gene by nucleic acid hybridization, and conducting an immunological assay for the detection of the R protein encoded by the R gene. It is recognized that oligonucleotide probes and PCR primers can be designed to identity the R genes of the present invention and that such probes and PCR primers can be utilized in methods disclosed elsewhere herein or otherwise known in the art to rapidly identify in a population of plants one or more plants comprising the presence of an R gene of the present invention.

Depending on the desired outcome, the polynucleotide constructs of the invention can be stably incorporated into the genome of the plant cell or not stably incorporated into genome of the plant cell. If, for example, the desired outcome is to produce a stably transformed plant with enhanced resistance to a plant disease caused by at least one race of a *Phytophthora* sp., then the polynucleotide construct can be, for example, fused into a plant transformation vector suitable for the stable incorporation of the polynucleotide construct into the genome of the plant cell. Typically, the stably transformed plant cell will be regenerated into a transformed plant that comprises in its genome the polynucleotide construct. Such a stably transformed plant is capable of transmitting the polynucleotide construct to progeny plants in subsequent generations via sexual and/or asexual reproduction. Plant transformation vectors, methods for stably transforming plants with an introduced polynucleotide construct and methods for plant regeneration from transformed plant cells and tissues are generally known in the art for both monocotyledonous and dicotyledonous plants or described elsewhere herein.

In other embodiments of the invention in which it is not desired to stably incorporate the polynucleotide construct in the genome of the plant, transient transformation methods can be utilized to introduce the polynucleotide construct into one or more plant cells of a plant. Such transient transformation methods include, for example, viral-based methods which involve the use of viral particles or at least viral nucleic acids. Generally, such viral-based methods involve constructing a modified viral nucleic acid comprising the a polynucleotide construct of the invention operably linked to the viral nucleic acid and then contacting the plant either with a modified virus comprising the modified viral nucleic acid or with the viral nucleic acid or with the modified viral nucleic acid itself. The modified virus and/or modified viral nucleic acids can be applied to the plant or part thereof, for example, in accordance with conventional methods used in agriculture, for example, by spraying, irrigation, dusting, or the like. The modified virus and/or modified viral nucleic acids can be applied in the form of directly sprayable solutions, powders, suspensions or dispersions, emulsions, oil dispersions, pastes, dustable products, materials for spreading, or granules, by means of spraying, atomizing, dusting, spreading or pouring. It is recognized that it may be desirable to prepare formulations comprising the modified virus and/or modified viral nucleic acids before applying to the plant or part or parts thereof. Methods for making pesticidal formulations are generally known in the art or described elsewhere herein.

The present invention provides nucleic acid molecules comprising R genes. Preferably, such R genes are capable of conferring upon a host plant, particularly a solanaceous host plant enhanced resistance to a plant disease caused by at least one race of a *Phytophthora* sp. Thus, such R genes find use in limiting a plant disease caused by at least one race of a *Phytophthora* sp. in agricultural production. The R genes of the present invention include, but are not limited to, the R genes whose nucleotide sequences are disclosed herein but also include orthologs and other variants that are capable of conferring to a plant resistance to a plant disease caused by at least one race of a *Phytophthora* sp. Methods are known in the art or otherwise disclosed herein for determining resistance of a plant a plant disease caused by at least one race of a *Phytophthora* sp., including, for example, the detached leaf assay utilizing detached *Nicotiana benthamiana* leaves that is described elsewhere herein.

The present invention further provides plants and cells thereof, particularly solanaceous plants and cells thereof, comprising Rpi-amr3i, that are produced by methods that do not involve the introduction of recombinant DNA into the plant or a cell thereof. Such methods can comprise, for example, interspecific hybridizations involving two or more different plant species. In certain embodiments, the solanaceous plant is any solanaceous plant except a *Solanum americanum* plant. In other embodiments, the solanaceous plants is any solanaceous plant except a *Solanum americanum* plant comprising Rpi-amr3i having the nucleotide sequence set forth in SEQ ID NO: 1.

Additionally provided are methods for introducing Rpi-amr3i into a solanaceous plant lacking in its genome Rpi-amr3i (SEQ ID NO: 1). The methods comprise crossing (i.e. cross-pollinating) a first solanaceous plant comprising in its genome at least one copy of Rpi-amr3i with a second solanaceous plant lacking in its genome Rpi-amr3i. The first and second solanaceous plants can be the same solanaceous species or can be different solanaceous species. For example, the first solanaceous plant can be *Solanum americanum* and the second solanaceous plant can be *Solanum tuberosum* or *Solanum lycopersicum.* Such a crossing of a first species of a plant to a second species of a plant is known as an interspecific hybridization and can be used to introgress a gene or genes of interest (e.g. Rpi-amr3i) from one species into a related species lacking the gene or genes of interest and typically involves multiple generations of backcrossing of the progeny with the related species and selection at each generation of progeny comprising the gene or genes of interest. Such interspecific hybridization, introgression, and backcrossing methods are well known in the art and can be used in the methods of the present invention. See "Principals of Cultivar Development," Fehr, 1993, Macmillan Publishing Company, New York; and "Fundamentals of Plant Genetics and Breeding," Welsh, 1981, John Wiley & Sons, Inc., New York.

In methods of the present invention for introducing Rpi-amr3i into a solanaceous plant lacking in its genome Rpi-amr3i, either the first solanaceous plant or the second solanaceous plant can be the the pollen donor plant. For example, if the first solanaceous plant is the pollen donor plant, then the second solanaceous plant is the pollen-recipient plant. Likewise, if the second solanaceous plant is the pollen donor plant, then the first solanaceous plant is the pollen-recipient plant. Following the crossing, the pollen-recipient plant is grown under conditions favorable for the growth and development of the plant and for a sufficient period of time for seed to mature or to achieve an otherwise desirable growth stage for use in a subsequent in vitro germination procedure such as, for example, embryo rescue that is described below. The seed can then be harvested and those seed comprising Rpi-amr3i identified by any method known in the art including, for example, the methods for identifying a solanaceous plant that displays newly conferred or enhanced resistance to a plant disease caused by at least one race of a *Phytophthora* sp. that are described elsewhere herein. In certain embodiments, the first solanaceous plant is a *Solanum americanum* plant comprising Rpi-amr3i and the second plant is *Solanum americanum* plant lacking Rpi-amr3i. In preferred embodiments, the first solanaceous plant is a *Solanum americanum* plant comprising Rpi-amr3i or other solanaceous plant species comprising in its genome Rpi-amr3i and the second solanaceous plant is solanaceous plant species other than *Solanum americanum*. Preferred solanaceous plants are potato, tomato, eggplant, pepper, tobacco, and petunia.

It is recognized, however, that in certain embodiments of the invention involving interspecific hybridizations, it may be advantageous to harvest the seed resulting from such interspecific hybridizations at an immature growth stage and then to germinate the immature seeds in culture (i.e. in vitro), whereby the seeds are allowed germinate in culture using methods known in art as "embryo rescue" methods. See Reed (2005) "Embryo Rescue," in *Plant Development and Biotechnology,* Trigiano and Gray, eds. (PDF). CRC Press, Boca Raton, pp. 235-239; and Sharma et al. (1996) *Euphytica* 89: 325-337. It is further recognized that "embryo rescue methods are typically used when mature seeds produced by an interspecific cross display little or no germination, whereby few or no interspecific hybrid plants are produced.

The methods of the present invention find use in producing plants with enhanced resistance to a plant disease caused by at least one race of at least one *Phytophthora* sp. Typically, the methods of the present invention will enhance or increase the resistance of the subject plant to the plant disease by at least 25%, 50%, 75% 100%, 150%, 200%, 250%, 500% or more when compared to the resistance of a control plant to the same race or races of *Phytophthora* sp. Unless stated otherwise or apparent from the context of a use, a control plant for the present invention is a plant that does not comprise the polynucleotide construct of the present invention. Preferably, the control plant is essentially identical (e.g. same species, subspecies, and variety) to the plant comprising the polynucleotide construct of the present invention except the control does not comprise the polynucleotide construct. In some embodiments, the control will comprise a polynucleotide construct but not comprise the one or more R gene sequences that are in a polynucleotide construct of the present invention.

Additionally, the present invention provides transformed plants, seeds, and plant cells produced by the methods of present invention and/or comprising a polynucleotide construct of the present invention. Also provided are progeny plants and seeds thereof comprising a polynucleotide construct of the present invention. The present invention also provides fruits, seeds, tubers, leaves, stems, roots, and other plant parts produced by the transformed plants and/or progeny plants of the invention as well as food products and other agricultural products comprising, or produced or derived from, the plants or any part or parts thereof including, but not limited to, fruits, tubers, leaves, stems, roots, and seed. Other agricultural products include, for example, smoking products produced from tobacco leaves (e.g., cigarettes, cigars, and pipe and chewing tobacco) and food and industrial starch products produced from potato tubers. It is recognized that such food products can be consumed or used by humans and other animals including, but not limited to, pets (e.g., dogs and cats), livestock (e.g., pigs, cows, chickens, turkeys, and ducks), and animals produced in freshwater and marine aquaculture systems (e.g. fish, shrimp, prawns, crayfish, and lobsters).

Non-limiting examples of the compositions and methods of the present invention are as follows:

1. A nucleic acid molecule comprising a nucleotide sequence selected from the group consisting of:
   (a) the nucleotide sequence set forth in SEQ ID NO: 1;
   (b) a nucleotide sequence encoding the amino acid sequence set forth in SEQ ID NO: 2, and optionally, wherein the nucleotide sequence is not naturally occurring;
   (c) the nucleotide sequence set forth in SEQ ID NO: 3;
   (d) a nucleotide sequence having at least 90% sequence identity to at least one of the nucleotide sequences set forth in SEQ ID NO: 1 and 3, wherein the nucleic acid molecule is capable of conferring resistance to a plant disease caused by at least one race of at least one *Phytophthora* sp. to a plant comprising the nucleic acid molecule and optionally, wherein the nucleotide sequence is not naturally occurring; and
   (e) a nucleic acid molecule comprising a nucleotide sequence encoding an amino acid sequence having at least 90% sequence identity to the amino acid sequence set forth in SEQ ID NO: 2, wherein the nucleic acid molecule is capable of conferring resistance to a plant disease caused by at least one race of at least one *Phytophthora* sp. to a plant comprising the nucleic acid molecule and optionally, wherein the nucleotide sequence is not naturally occurring.
2. The nucleic acid molecule of embodiment 1, wherein the nucleic acid molecule is an isolated nucleic acid molecule.
3. An expression cassette comprising the nucleic acid molecule of embodiment 1 or 2 and an operably linked heterologous promoter.
4. A vector comprising the nucleic acid molecule of embodiment 1 or 2 or the expression cassette of embodiment 3.
5. A vector of embodiment 4, further comprising an additional R gene.
6. A host cell transformed with the nucleic acid molecule of embodiment 1 or 2, the expression cassette of embodiment 3, or the vector of embodiment 4 or 5.
7. The host cell of embodiment 6, wherein the host cell is a plant cell, a bacterium, a fungal cell, or an animal cell.
8. The host cell of embodiment 6 or 7, wherein the host cell is a solanaceous plant cell.
9. A plant or plant cell comprising the nucleic acid molecule of embodiment 1 or 2, the expression cassette of embodiment 3, or the vector of embodiment 4 or 5.
10. The plant or plant cell of embodiment 9, wherein the plant is a solanaceous plan and the plant cell is a solanaceous plant cell t.
11. The plant of embodiment 10, wherein the solanaceous plant is not *Solanum americanum* and the solanaceous plant is selected from the group consisting of potato, tomato, eggplant, pepper, tobacco, and petunia.
12. A transgenic plant comprising stably incorporated in its genome a polynucleotide construct comprising a nucleotide sequence selected from the group consisting of:
   (a) the nucleotide sequence set forth in SEQ ID NO: 1;
   (b) a nucleotide sequence encoding the amino acid sequence set forth in SEQ ID NO: 2;
   (c) the nucleotide sequence set forth in SEQ ID NO: 3;
   (d) a nucleotide sequence having at least 90% sequence identity to at least one of the nucleotide sequences set forth in SEQ ID NO: 1 and 3, wherein the nucleic acid molecule is capable of conferring resistance to a plant disease caused by at least one race of at least one *Phytophthora* sp. to a plant comprising the nucleic acid molecule; and (e) a nucleic acid molecule comprising a nucleotide sequence encoding an amino acid sequence having at least 90% sequence identity to the amino acid sequence set forth in SEQ ID NO: 2, wherein the nucleic acid molecule is capable of conferring resistance to a plant disease caused by at least one race of at least one *Phytophthora* sp. to a plant comprising the nucleic acid molecule.

13. The transgenic plant of embodiment 12, wherein the polynucleotide construct comprises the nucleotide sequence of any one of (b)-(e) and further comprises a promoter operably linked for the expression of the nucleotide sequence in a plant.

14. The transgenic plant of embodiment 13, wherein the promoter is selected from the group consisting of pathogen-inducible, constitutive, tissue-preferred, wound-inducible, and chemical-regulated promoters.

15. The transgenic plant of embodiment any one of embodiments 12-14, wherein the transgenic plant is a solanaceous plant.

16. The transgenic plant of embodiment any one of embodiments 12-15, wherein the solanaceous plant is selected from the group consisting of potato, tomato, eggplant, pepper, tobacco, and petunia.

17. The transgenic plant of any one of embodiments 12-16, wherein the transgenic plant comprises enhanced resistance to a plant disease caused by at least one race of at least one *Phytophthora* sp., relative to a control plant.

18. The transgenic plant of embodiment 17, wherein the transgenic plant comprises enhanced resistance to late blight caused by at least one race of *Phytophthora infestans,* relative to a control plant.

19. The transgenic plant of any one of embodiments 12-18, wherein the transgenic plant is a potato or tomato plant.

20. A method for enhancing the resistance of a plant to a plant disease caused by at least one race of at least one *Phytophthora* sp., the method comprising introducing a polynucleotide construct into at least one plant cell, the polynucleotide construct comprising a nucleotide sequence selected from the group consisting of:

(a) the nucleotide sequence set forth in SEQ ID NO: 1;

(b) a nucleotide sequence encoding the amino acid sequence set forth in SEQ ID NO: 2;

(c) the nucleotide sequence set forth in SEQ ID NO: 3;

(d) a nucleotide sequence having at least 90% sequence identity to at least one of the nucleotide sequences set forth in SEQ ID NO: 1 and 3, wherein the nucleic acid molecule is capable of conferring resistance to a plant disease caused by at least one race of at least one *Phytophthora* sp. to a plant comprising the nucleic acid molecule; and (e) a nucleic acid molecule comprising a nucleotide sequence encoding an amino acid sequence having at least 90% sequence identity to the amino acid sequence set forth in SEQ ID NO: 2, wherein the nucleic acid molecule is capable of conferring resistance to a plant disease caused by at least one race of at least one *Phytophthora* sp. to a plant comprising the nucleic acid molecule.

21. The method of embodiment 20, wherein the polynucleotide construct is stably incorporated into the genome of the plant cell.

22. The method of embodiment 20 or 21, wherein the plant cell is regenerated into a plant comprising in its genome the polynucleotide construct.

23. The method of any one of embodiments 20-22, wherein the polynucleotide construct comprises the nucleotide sequence of any one of (b)-(e) and further comprises a promoter operably linked for the expression of the nucleotide sequence in a plant.

24. The method of embodiment 23, wherein the promoter is selected from the group consisting of pathogen-inducible, constitutive, tissue-preferred, wound-inducible, and chemical-regulated promoters.

25. The method of any one of embodiments 20-24, wherein the plant comprising the polynucleotide construct comprises enhanced resistance to a plant disease caused by at least one race of at least one *Phytophthora* sp., relative to a control plant.

26. The method of embodiment 25, wherein the plant comprises enhanced resistance to late blight caused by at least one race of *Phytophthora infestans,* relative to a control plant.

27. The method of any one of embodiments 20-26, wherein the plant is a potato or a tomato plant.

28. A plant produced by the method of any one of embodiments 20-27.

29. A fruit, tuber, leaf, or seed of the plant of any one of embodiments 9-19 and 28, wherein the fruit, tuber, leaf or seed comprises the polynucleotide construct.

30. A method of limiting a plant disease caused by at least one race of at least one *Phytophthora* sp. in agricultural crop production, the method comprising planting a seedling, tuber, or seed of the plant of any one of embodiments 9-19 and 28 and growing the seedling, tuber, or seed under conditions favorable for the growth and development of a plant resulting thereform, wherein the seedling, tuber, or seed comprises the nucleic acid molecule, expression cassette, vector, or polynucleotide construct.

31. The method of embodiment 30, further comprising harvesting at least one fruit, tuber, leaf and/or seed from the plant.

32. Use of the plant, tuber, or seed of any one of embodiments 9-19, 28, 29, and 41-45 in agriculture.

33. A human or animal food product comprising, or produced using, the plant, fruit, tuber, leaf, and/or seed of any one of embodiments 9-19, 28, 29, and 41-45.

34. A polypeptide comprising an amino acid sequence selected from the group consisting of:

(a) the amino acid sequence encoded by the nucleotide sequence set forth in SEQ ID NO: 1;

(b) the amino acid sequence set forth in SEQ ID NO: 2;

(c) the amino acid sequence encoded by the nucleotide sequence set forth in SEQ ID NO: 3; and (d) an amino acid sequence having at least 90% sequence identity to the amino acid sequence set forth in SEQ ID NO: 2, wherein a polypeptide comprising the amino acid sequence is capable of conferring resistance to a plant disease caused by at least one race of at least one *Phytophthora* sp. to a plant comprising the polypeptide.

35. A method for identifying a solanaceous plant that displays newly conferred or enhanced resistance to a plant disease caused by at least one race of at least one *Phytophthora* sp., the method comprising detecting in the plant, or in at least one part or cell thereof, the presence of Rpi-amr3i.

36. The method of embodiment 35, wherein the plant disease is late blight caused by at least one race of *Phytophthora infestans*. 37. The method of embodiment 35 or 36, wherein the solanaceous plant is a potato or tomato plant.

38. The method of any one of embodiments 35-37, wherein the presence of Rpi-amr3i is detected by detecting at least one marker within Rpi-amr3i.

39. The method of any one of embodiments 35-38, wherein Rpi-amr3i comprises or consists of the nucleotide sequence set forth in SEQ ID NO: 1.

40. The method of any one of embodiments 35-39, wherein detecting the presence of Rpi-amr3i comprises a member selected from the group consisting of PCR amplification, nucleic acid sequencing, nucleic acid hybridization, and an immunological assay for the detection of the R protein encoded by Rpi-amr3i.

41. A solanaceous plant identified by the process of any one of embodiments 35-40.

42. The solanaceous plant of embodiment 40, wherein the solanaceous plant is not *Solanum americanum.*

43. A seed of the solanaceous plant of embodiment 41 or 42.

44. A plant or plant cell comprising Rpi-amr3i, wherein the plant is not a *Solanum americanum* plant and the plant cell is not an *Solanum americanum* plant cell.

45. The plant or plant cell of embodiment 44, wherein the plant is a solanaceous plant and the plant cell is a solanaceous plant cell.

Additional embodiments of the methods and compositions of the present invention are described elsewhere herein.

Preferred plants of the invention are solanaceous plants. As used herein, the term "solanaceous plant" refers to a plant that is a member of the Solanaceae family. Such solanaceous plants include, for example, domesticated and non-domesticated members of Solanaceae family. Solanaceous plants of the present invention include, but are not limited to, potato (*Solanum tuberosum*), eggplant (*Solanum melongena*), petunia (*Petunia* spp., e.g., *Petunia* x *hybrida* or *Petunia hybrida*), *Physalis* sp., woody nightshade (*Solanum dulcamara*), garden huckleberry (*Solanum scabrum*), gboma eggplant (*Solanum macrocarpon*), pepper (*Capsicum* spp; e.g., *Capsicum annuum, C. baccatum, C. chinense, C. frutescens, C. pubescens,* and the like), tomato (*Solanum lycopersicum* or *Lycopersicon esculentum*), tobacco (*Nicotiana* spp., e.g. *N. tabacum, N. benthamiana*), *Solanum americanum, Solanum demissum, Solanum stoloniferum, Solanum papita, Solanum bulbocastanum, Solanum edinense, Solanum schenckii, Solanum hjertingii, Solanum venturi, Solanum mochiquense, Solanum chacoense,* and *Solanum pimpinellifolium.* In preferred embodiments, the solanaceous plants are solanaceous plants grown in agriculture including, but not limited to, potato, tomato, eggplant, pepper, tobacco and petunia. In more preferred embodiments, the solanaceous plants are potato and tomato. In even more preferred embodiments, the preferred plant is potato. In certain other embodiments, the preferred solanaceous are all solanaceous plants except for *Solanum americanum.*

The term "solanaceous plant" is intended to encompass solanaceous plants at any stage of maturity or development, as well as any cells, tissues or organs (plant parts) taken or derived from any such plant unless otherwise clearly indicated by context. Solanaceous plant parts include, but are not limited to, fruits, stems, tubers, roots, flowers, ovules, stamens, leaves, embryos, meristematic regions, callus tissue, anther cultures, gametophytes, sporophytes, pollen, microspores, protoplasts, and the like. The present invention also includes seeds produced by the solanaceous plants of the present invention.

The composition and methods of the present invention find us in producing plants with enhanced resistance to at least one race of at least one *Phytophthora* sp. In preferred embodiments of the invention, the *Phytophthora* sp. is *Phytophthora infestans.* In other embodiments, the *Phytophthora* sp. is a *Phytophthora* sp. that is capable of causing a plant disease on at least one plant. For the present invention, *Phytophthora* spp. include, but are not limited to, *Phytophthora infestans, Phytophthora parasitica, Phytophthora ramorum, Phytophthora ipomoeae, Phytophthora mirabilis, Phytophthora capsici, Phytophthora porri, Phytophthora sojae, Phytophthora palmivora,* and *Phytophthora phaseoli.*

In one embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in SEQ ID NO: 1 or to a fragment thereof. In another embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in SEQ ID NO: 3 or to a fragment thereof.

The present invention encompasses isolated or substantially purified polynucleotide (also referred to herein as "nucleic acid molecule", "nucleic acid" and the like) or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

In certain embodiments of the invention, the fragments and variants of the disclosed polynucleotides and proteins encoded thereby are those that are capable of conferring to a plant resistance to a plant disease caused by at least one race of at least one *Phytophthora* sp. Preferably, a polynucleotide comprising a fragment of a native R polynucleotide of the present invention is capable of conferring resistance to a plant disease caused by at least one race of at least one *Phytophthora* sp. to a plant comprising the polynucleotide. Likewise, a protein or polypeptide comprising a native R protein of the present invention is preferably capable of conferring resistance to a plant disease caused by at least one race of at least one *Phytophthora* sp. to a plant comprising the protein or polypeptide.

Polynucleotides that are fragments of a native R polynucleotide comprise at least 16, 20, 50, 75, 100, 125, 150, 175, 200, 250, 300, 350, 400, 450, 500, 550, or 575 contiguous nucleotides, or up to the number of nucleotides present in a full-length R polynucleotide disclosed herein (for example, 5352 and 2661 nucleotides for of SEQ ID NOS: 1 and 3, respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 75%, 80%, 85%, 90%, 91%, 92%, 93%, 94%, 95%, 96%, 97%, 98%, 99% or more sequence identity to at least one nucleotide sequence selected from the group consisting of SEQ ID NOS: 1 and 3, and optionally comprise a non-naturally occurring nucleotide sequence that differs from the nucleotide sequence set forth in SEQ ID NO: 1 and/or 3 by at least one nucleotide modification selected from the group consisting of the substitution of at least one nucleotide, the addition of at least one nucleotide, and the deletion of at least one nucleotide. It is understood that the addition of at least one nucleotide can be the addition of one or more nucleotides within a nucleotide sequence of the present invention (e.g. SEQ ID NO: 1 or 3), the addition of one or more nucleotides to the 5' end of a nucleotide sequence of the present invention, and/or the addition of one or more nucleotides to the 3' end of a nucleotide sequence of the present invention.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptide of SEQ ID NO: 2 and 4 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity. In certain embodiments of the invention, variants of a particular polypeptide of the invention will have at least about 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 2, and optionally comprises a non-naturally occurring amino acid sequence that differs from the amino acid set forth in SEQ ID NO: 2 by at least one amino acid modification selected from the group consisting of the substitution of at least one amino acid, the addition of at least one amino acid, and the deletion of at least one amino acid. It is understood that the addition of at least one amino acid can be the addition of one or more amino acids within an amino acid sequence of the present invention (e.g. SEQ ID NO: 2), the addition of one or more amino acids to the N-terminal end of an amino acid sequence of the present invention, and/or the addition of one or more amino acids to the C-terminal end of an amino acid sequence of the present invention.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 75%, 80%, 85%, 90%, 91%, 92%, 93%, 94%, 95%, 96%, 97%, 98%, 99% or more sequence identity to the amino acid sequence for the native protein (e.g. the amino acid sequence set forth in SEQ ID NO: 2) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass both naturally occurring proteins as well as variations and modified forms thereof, More preferably, such variants confer to a plant or part thereof comprising the variant enhanced resistance a plant disease caused by at least one race of at least one *Phytophthora* sp. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. “Orthologs” is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode R proteins and which hybridize under stringent conditions to at least one of the R proteins disclosed herein or otherwise known in the art, or to variants or fragments thereof, are encompassed by the present invention.

In one embodiment, the orthologs of the present invention have coding sequences comprising at least 80%, 85%, 90%, 91%, 92%, 93%, 94%, 95%, 96%, 97%, 98%, 99%, or greater nucleotide sequence identity to a nucleotide sequence selected from the group consisting of the nucleotide sequences set forth in SEQ ID NO: 1 and SEQ ID NO: 3 and/or encode proteins comprising least 80%, 85%, 90%, 91%, 92%, 93%, 94%, 95%, 96%, 97%, 98%, 99%, or greater amino acid sequence identity to an amino acid sequence selected from the group consisting of the amino acid sequences set forth in SEQ ID NO: 2.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among the sequence of the gene or cDNA of interest sequences and are optimally at least about 10 nucleotides in length, and most optimally at least about 20 nucleotides in length. Such probes may be used to amplify corresponding polynucleotides for the particular gene of interest from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.). An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the R protein coding sequences of the present invention encompass polynucleotide molecules comprising a nucleotide sequence that is sufficiently identical to the nucleotide sequence of any one or more of SEQ ID NOS: 1 and 3. The term “sufficiently identical” is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. BLAST, Gapped BLAST, and PSI-Blast, XBLAST and NBLAST are available on the World Wide Web at ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the World Wide Web at ebi.ac.uk/Tools/clustalw/index).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide constructs comprising R protein coding regions can be provided in expression cassettes for expression in the plant or other organism or non-human host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e., a promoter), a R protein coding region of the invention, and a transcriptional and translational termination region (i.e., termination region) functional in plants or other organism or non-human host cell. The regulatory regions (i.e., promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule, polynucleotide, nucleotide sequence, or polynucleotide construct is a nucleic acid molecule, polynucleotide, nucleotide sequence, or polynucleotide construct that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The present invention provides host cells comprising at least of the nucleic acid molecules, expression cassettes, and vectors of the present invention. In preferred embodiments of the invention, a host cells is plant cell. In other embodiments, a host cell is selected from the group consisting of a bacterium, a fungal cell, and an animal cell. In certain embodiments, a host cell is non-human animal cell. However, in some other embodiments, the host cell is an in-vitro cultured human cell.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e., foreign or heterologous to the promoter, the R protein of interest, and/or the plant host), or any combination thereof. Convenient termination regions are available from the Ti-plasmid of *A. tumefaciens,* such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gown (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA,* ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the polynucleotide constructs of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon,* pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology,* Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An, G. et al. (1986) *Plant Pysiol.,* 81:301-305; Fry, J., et al. (1987) *Plant Cell Rep.* 6:321-325; Block, M. (1988) *Theor. Appl Genet.*76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) Bio/Technol. 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; *Guo Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J* 5:299-307; Borkowska et al. (1994) *Acta. Physiol Plant.* 16:225-230; Christou, P. (1994) *Agro. Food. Ind. Hi Tech.* 5:17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant. It is recognized that stable and transient transformation methods comprise introducing one or more nucleic acid molecules (e.g. DNA), particularly one or more recombinant nucleic acid molecules (e.g. recombinant DNA) into a plant, plant cell, or other host cell or organism.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100:247-250; Scheid et al., (1991) *Mol. Gen. Genet.,* 228:104-112; Guerche et al., (1987) *Plant Science* 52: 111-116; Neuhause et al., (1987) *Theor. Appl Genet.* 75:30-36; Klein et al., (1987) *Nature* 327:70-73; Howell et al., (1980) *Science* 208:1265; Horsch et al., (1985) *Science* 227: 1229-1231; DeBlock et al., (1989) *Plant Physiology* 91:694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues,* ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

In specific embodiments, the polynucleotide constructs and expression cassettes of the invention can be provided to a plant using a variety of transient transformation methods known in the art. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

Any methods known in the art for modifying DNA in the genome of a plant can be used to modify genomic nucleotide sequences in planta, for example, to create or insert a resistance gene or even to replace or modify an endogenous resistance gene or allele thereof Such methods include, but are not limited to, genome editing techniques, such as, for example, methods involving targeted mutagenesis, homologous recombination, and mutation breeding. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing double breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J Mol Biol* 355:443-58; Ashworth et al., (2006) *Nature* 441:656-9; Doyon et al. (2006) *J Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) *Virulence* 1:428-432; Christian et al. *Genetics* (2010) 186: 757-761; Li et al. (2010) *Nuc. Acids Res.* (2010) doi: 10.1093/nar/gkq704; and Miller et al. (2011) *Nature Biotechnology* 29:143-148; all of which are herein incorporated by reference.

The CRISPR/Cas nuclease system can also be used to make double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho S. W. et al., Nat. Biotechnol. 31:230-232, 2013; Cong L. et al., Science 339:819-823, 2013; Mali P. et al., Science 339:823-826, 2013; Feng Z. et al., Cell Research: 1-4, 2013).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov F. D. et al., Nat Rev Genet. 11:636-46, 2010; Carroll D., Genetics. 188:773-82, 2011).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

The nucleic acid molecules, expression cassettes, vectors, and polynucleotide constructs of the present invention may be used for transformation of any plant species, including, but not limited to, monocots and dicots.

As used herein, the term "plant" includes seeds, plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

As used herein, the terms "transgenic plant" and "transformed plant" are equivalent terms that refer to a "plant" as described above, wherein the plant comprises a heterologous nucleic acid molecule, heterologous polynucleotide, or heterologous polynucleotide construct that is introduced into a plant by, for example, any of the stable and transient transformation methods disclosed elsewhere herein or otherwise known in the art. Such transgenic plants and transformed plants also refer, for example, the plant into which the heterologous nucleic acid molecule, heterologous polynucleotide, or heterologous polynucleotide construct was first introduced and also any of its progeny plants that comprise the heterologous nucleic acid molecule, heterologous polynucleotide, or heterologous polynucleotide construct.

In certain embodiments of the invention, the methods involve the planting of seedlings and/or tubers and then growing such seedlings and tubers so as to produce plants derived therefrom and optionally harvesting from the plants a plant part or parts. As used herein, a "seedling" refers to a less than fully mature plant that is typically grown in greenhouse or other controlled- or semi-controlled (e.g. a cold frame) environmental conditions before planting or replanting outdoors or in a greenhouse for the production a harvestable plant part, such as, for example, a tomato fruit, a potato tuber or a tobacco leaf. As used herein, a "tuber" refers to an entire tuber or part or parts thereof, unless stated otherwise or apparent from the context of use. A preferred tuber of the present invention is a potato tuber.

In the methods of the invention involving planting a tuber, a part of tuber preferably comprises a sufficient portion of the tuber whereby the part is capable of growing into a plant under favorable conditions for the growth and development of a plant derived from the tuber. It is recognized that such favorable conditions for the growth and development of crop plants, particularly solanaceous crop plants, are generally known in the art.

In some embodiments of the present invention, a plant cell is transformed with a polynucleotide construct encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of polynucleotide constructs and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for enhancing the resistance of a plant to plant disease, particularly to compositions and methods for enhancing the resistance of a plant to a plant disease caused by at least one race of at least one *Phytophthora* sp. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

The following examples are offered by way of illustration and not by way of limitation.

EXAMPLES

Example 1

*Solanum americanum* is a Rich Source of Late Blight Resistance Genes

We set out to investigate the immune response towards *P. infestans* in a set of *S. americanum* (2n) and *S. nigrum* (6n) accessions obtained from three European seed collections (Table 1). Flow cytometry analyses identified that accessions 944750095, A54750014 and A14750006, originally listed as *S. nigrum,* were diploid, rather than hexaploid (data not shown). This is in accordance with previously reported frequent misidentification between *S. nigrum* and *S. americanum* (Manoko et al. (2007) *Plant Syst. Evol.* 267:1-11). For the purposes of the present invention, all plant accessions will be referred as belonging to *S. americanum* sensu latu group, unless stated otherwise or apparent from the context of usage. Furthermore it is recognized the present invention does not depend on the R genes of the present invention being isolated from a particular plant species or even that the species is in the genus *Solanum.* Moreover, the present invention provides both naturally occurring and non-naturally (i.e synthetic or artificial) R genes that provide resistance to late blight disease, particularly to potato late blight disease.

TABLE 1

*Solanum* Accessions

| Accession | Species | Place of origin[2] | Source[1] | Phenotype | No. of R genes based on F2 segregation pattern |
|---|---|---|---|---|---|
| 954750186 | *S. americanum* | Brazil | RU | Susceptible | — |
| 954750184 | *S. americanum* var. *Patulum* | unknown | RU | Resistant | 1 |
| 954750174 | *S. americanum* | unknown | RU | Resistant | 1 |
| A14750006 | Unclassified | unknown | RU | Resistant | 1 |
| 944750095 | Unclassified | Mexico | RU | Resistant | 2 or more |
| A54750014 | Unclassified | unknown | RU | Resistant | 2 or more |
| SOLA 140 | *S. americanum* | Cuba | IPK | Resistant | 2 or more |
| SOLA 424 | *S. americanum* | Middle America | IPK | Resistant | 2 or more |
| SOLA 428 | *S. americanum* | Middle America | IPK | Resistant | 2 or more |
| SOLA 432 | *S. americanum* | Middle America | IPK | Resistant | 2 or more |

TABLE 1-continued

| Solanum Accessions | | | | | |
|---|---|---|---|---|---|
| Accession | Species | Place of origin[2] | Source[1] | Phenotype | No. of R genes based on F2 segregation pattern |
| 10145 | *S. americanum* | El Salvador | NHM | Resistant | 1 |
| Wang 2059 | *S. americanum* | China | NHM | Resistant | 1 |
| Wang 2058 | *S. americanum* | China | NHM | Resistant | 1 |

[1]RU—Radboud University, Nijmegen, The Netherlands; IPK—IPK Gatersleben, Germany and NHM—Natural History Museum, London, United Kingdom.
[2]Middle America is a region comprising the southern portion of North American and the northern portion of South American and includes Mexico, Belize, Costa Rica, El Salvador, Guatemala, Honduras, Nicaragua, Panama, Colombia and Venezuela.

Pathogen susceptibility was assessed in detached leaf assays (DLAs), using four highly virulent *P. infestans* races (06_3928A, 88069, EC1 and NL07434). Accession 954750186 was susceptible to all tested races (supporting mycelial growth and sporulation). All other accessions remained fully resistant, with no visible sign of infection or only small sites of hypersensitive response (HR) in the form of local cell death at the site of *P. infestans* inoculation (FIG. 1).

To determine the genetic basis of *S. americanum* resistance, we crossed all resistant accessions as male parents to the susceptible line 954750186. Heterozygous F1 progeny showed no segregation for resistance to *P. infestans* races 06_3928A and EC1 (6-8 plants were tested for each F1), and were allowed to self-pollinate to generate F2 populations. We tested 60 to 100 plants per F2 for the response to 06_3928A and EC1 and found that the progeny of six F1 crosses segregated in a ratio suggesting the presence of a single (semi) dominant resistance gene (fitting 3:1 or 2:1). A further six crosses showed 15:1 segregation or no segregation at all (all plants resistant), suggesting the presence of two or more unlinked R genes (Table 1). An F2 population resulting from one of the crosses (954750186×944750095) was selected for R gene identification.

Example 2

RenSeq Mapping Reveals that Rpi-amr3 Maps Near R2 on Potato Chromosome 4

Pathogen inoculations on leaves of young F2 plants (F1 954750186×944750095) revealed 99 resistant and 6 susceptible plants (15:1 segregation), suggesting the presence of two unlinked dominant Rpi genes. To separate the genes, we self-pollinated 15 resistant F2 plants and determined the resistance segregation pattern in 30-200 F3 progeny. Four populations segregated 3:1 in DLA tests on leaves from young plants (8-10 weeks old). Interestingly, this result was not consistent in older plants, suggesting the presence of an additional resistance gene functional in adult plants (more than 12 weeks old) that were scored as susceptible when young.

We hypothesized that the underlying late blight resistance genes encode NB-LRR/NLR proteins. We applied RenSeq to resistant (R) and susceptible (S) parents, and to bulked DNA of the 50 most susceptible plants, including the 6 originally identified susceptible F2s, and additional susceptible plants in the progeny of the 15 resistant F2 plants (bulk susceptible, BS). MiSeq sequencing reads of the NLR enriched libraries were used to call and compare polymorphisms between the samples and the potato reference genome (The Potato Genome Sequencing Consortium (2011) *Nature* 475:189-195). We de novo assembled R parent RenSeq reads and used the assembly as reference to map R, S and BS RenSeq reads. To find linked contigs, we called homozygous SNPs between R and S parents that were absent in BS (less than 5% R allele; Jupe et al. (2013) *Plant J.* 76:530-544). Using BLAST to position candidate contigs to the doubled monoploid (DM) reference genome (>80% identity >1 kb), we found linkage to the interval on chromosome 4 (Ch4), between 3.5-8.5 Mb (in the DM haplotype, see FIG. 2, part a for details). We named the underlying resistance gene Rpi-amr3. This interval contains 3 NLR clusters (R2/Rpi-blb3, C17 and C18) on the physical map of the DM genome (30, 7 and 10 NLRs, respectively; Jupe et al. (2013) *Plant J.* 76:530-544). While no functional resistance genes has yet been described from C17 and C18, the R2 and Rpi-blb3 gene confer race-specific resistance against many, but not all, *P. infestans* races.

The genome of *S. americanum* is distantly related to the available sequenced DM potato genome. Thus, marker development based on reference information is hampered by large number of polymorphisms and genome rearrangements. To facilitate development of markers flanking each NLR cluster in the mapping interval, we Illumina-sequenced whole genomes of R and S parental lines (Whole Genome Shotgun sequencing, WGS) and de novo assembled R parent WGS reads. We anchored assembled contigs to the reference DM genome using BLAST (>80% identity, >2kb), selected contigs flanking each NLR cluster and converted them into CAPS markers (Konieczny and Ausubel (1993) *Plant J.* 4:403-10) based on WGS data from R and S parent using standard methods as described in Jupe et al. ((2013) *Plant J.* 76:530-544) and calling homozygous SNPs (FIG. 2, part a). Based on the initial 50 susceptible plants (used to create BS) we found that two markers, R2l_ 1_4 at 3.59 Mb and R2l_2_4 at 8.69) showed recombination between genotype and phenotype, while the remaining markers co-segregated with resistance.

To increase the number of recombination events within the candidate region and resolve the complex NLR cluster structure, we created a larger mapping population by back-crossing a resistant F1 plant to the susceptible line 954750186 (female parent). Eight resistant (DLA) $BC_1F_1$ plants that were heterozygous for both flanking markers were selected and self-pollinated. We screened 60-100 plants of eight $BC_1F_2$ populations with race 06_3928A and found that two (SP3534 and SP3543) segregate 3:1 for resistance, suggesting a single dominant gene. We further increased the number of plants in both populations to 210 and 195, respectively, and phenotyped all these plants with 06_3928A. We genotyped all plants with flanking markers and found 51 recombinants. These plants were further genotyped with marker R2l_2_5, which physically separates the two large NLR cluster R2/Rpi-blb3 and C18 (FIG. 2, part b). This confirmed that Rpi-amr3 belongs to the C18 cluster of CC-NBS-LRR genes positioned between 7.7-7.9 Mb (in the DM haplotype) on Ch 4 (FIG. 2, part b).

Example 3

RenSeq Combined with PacBio Sequencing Enables Assembly of Full-Length Sequences for 14 Co-Segregating Full-Length NLR Genes A major driver for this project was to establish an R gene cloning method that does not require construction of BAC libraries. We previously found that the high copy numbers and sequence similarity of NLR genes complicates de novo assembly of short Illumina RenSeq reads (Jupe et al. (2013) *Plant J.* 76:530-544; Andolfo et al. (2014) *BMC Plant Biol.* 14:120). We therefore explored NLR enrichment in combination with longer read technology offered by the PacBio RSII (Eid et al. (2008) *Science* 323:133-138). We used our *Solanum* NLR bait library (Jupe et al. (2013) *Plant J.* 76:530-544) to capture the full NLR complement from two independent libraries (1.5 kb and 2.5 kb gDNA fragments) derived from the Rpi-amr3-carrying parental accession 944750095 (see Methods for details). Sequencing 1.5 kb and 2.5 kb fractions on one and two SMRT cells, respectively, resulted in a total of 70.6 k Reads of Inserts (ROI). Analysis of these with the published NLR motif alignment and search tool (MAST) in combination with the NLR-parser (Jupe et al. (2012) *BMC Genomics* doi:10.1186/1471-2164-13-75; Jupe et al. (2013) *Plant J.* 76:530-544; Steuernagel et al. (2015) *Bioinformatics* 10.1093/bioinformatics/btv005) revealed that over 21.5 ROIs (30%) derive from NLRs, and 1030 (~5%) reads harbor full length NLR coding sequences. Subsequent de novo assembly of the NLR selected ROIs generated 323 full length and 311 partial NLRs (Steuernagel et al. (2015) *Bioinformatics* 10.1093/bioinformatics/btv005). We found 11 sequences (single ORF, full-length cds), and 10 truncated or partial NLRs to be potential *S. americanum* C18 homologs (>80% identity >1 kb). The correction of homopolymers in partial NLRs identified an additional three full-length C-18 NLR genes (FIG. 2, part c). Mapping cDNA RenSeq data to all de novo assembled genes using stringent conditions (Rallapalli et al. (2014) *BMC Genomics* 15:341; Andolfo et al. (2014) *BMC Plant Biol.* 14:120) identified six of the candidates to be highly expressed with a uniform coverage over the whole sequence. We further confirmed co-segregation of four of these sequences using gene specific markers (Rpi-amr3a, Rpi-amr3i, Rpi-amr3j and Rpi-amr3k) and for two we could not develop specific CAPS markers (Rpi-amr3b and Rpi-amr3l). Thus, RenSeq in conjunction with PacBio enabled us to rapidly identify co-segregating candidate resistance genes in a rapid and cost-efficient manner.

Example 4

Transient Expression of Five Co-Segregating Expressed NLR Genes in *Nicotiana benthamiana* Reveals one that Confers *P. infestans* Resistance We cloned the open reading frames of the six candidate NLRs into a binary expression vector under control of a 35S promoter and transformed into *Agrobacterium*. These constructs were transiently expressed in *N. benthamiana* detached leaves and inoculated with the *P. infestans* race 88069 (24 hours post infiltration), routinely used for transient assays in *N. benthamiana* plants as described in Lokossou et al. ((2009) *MPMI* 22:661) and Saunders et al. ((2012) *Plant Cell* 24: 3420). *P. infestans* growth was observed 6 days post inoculation (dpi) on GFP-infiltrated control leaves and all other constructs, except for the R2 control and the candidate gene Rpi-amr3i. 35S: Rpi-amr3i infiltrated leaves remained symptomless until 15 dpi (FIG. 3). Transient delivery of candidate Rpi-amr3i under its native promoter and terminator elements (2 kb 5' and 1 kb 3', nucleotides 1 to 1918 and 4583 to 5352, respectively, of SEQ ID NO: 1) followed by *P. infestans* infection showed the same level of resistance as the 35S:Rpi-amr3i construct (FIG. 4). This transient expression system identified candidate Rpi-amr3i as the functional Rpi-amr3 gene.

Example 5

Stable Transformed Potato Lines Carrying 35S:Rpi-amr3 Resist Diverse *P. infestans* Races We created stable transgenic plants with 35S:Rpi-amr3 constructs in diploid homozygous Solynta Research line nr 26 (available on the World Wide Web at solynta.com) using the transformation method described in Kumar et al. ((2009) *Plant J.* 9:147). This 35S:Rpi-amr3 construct comprises nucleotides 1858 to 4688 of SEQ ID NO: 1. Transgenic plants were tested in a detached leaf assay (DLA) as described by Foster et al. ((2009) *MPMI* 22:589-600) and showed resistance against diverse *P. infestans* races, including 88069, 06_3928A, EC3527, EC3626 and MP324. (FIG. 5). In contrast all four lines carrying non-functional Rpi-amr3 paralogs remained fully susceptible to tested *P. infestans* races (data not shown). This result confirms that the cloned gene is the functional Rpi-amr3 gene conferring resistance against multiple races of *P. infestans* in planta.

Example 6

Rpi-amr3 is a Member of a Multigene Family Linked to But Distantly Related to R2

The Rpi-amr3 2,664 bp ORF encodes a protein sequence of 887 amino acids (SEQ ID NO: 2). It contains typical characteristics of a CC-NB-LRR class resistance protein; this is coiled-coil domain (CC, 1-115aa), nucleotide binding domain (NB-ARC 151-433aa) and seven leucine-rich repeats (LRR, 500-800aa).

Example 7

Stable Transformed Potato Lines Carrying Rpi-amr3 and Testing for Resistance to Diverse *P. infestans* Races Transformed potato plants were produced by transforming Solynta Research line nr 26 and Maris Piper with the full-length Rpi-amr3 gene (SEQ ID NO: 1) comprising the native promoter, open reading frame and terminator regions using a stable transformation method for potato as described in in Kumar et al. ((2009) *Plant J.* 9:147). For the transformations, the Rpi-amr3 sequence was incorporated into the binary expression vector pICSLUS0001. Individual transgenic Solynta 26 (FIG. 6) and Maris Piper (FIG. 7) potato plants ($T_0$) comprising Rpi-amr3 were tested for resistance to *P. infestans* race 88069 in the detatched leaf assay described above and compared to the resistance of control untransformed potato plants in the case of Maris Piper, or a transformed line comprising a non-functional Rpi-amr3 paralog in the case of Solynta nr 26. In both cases, control plants showed large necrotic lesions and sporulation of the pathogen, whereas lines expressing Rpi-amr3 showed a resistant phenotype consisting of a weak or no hypersensitive defense response at the site of infection and no necrotic lesions or sporulation.

Individual transgenic potato plants expressing Rpi-amr3 are expected to show enhanced resistance to multiple races of *P. infestans,* including 06_3928A, EC3527, EC3626 and MP324.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A transgenic solanaceous plant or plant cell comprising stably incorporated in its genome a heterologous polynucleotide comprising a nucleotide sequence selected from the group consisting of:

(a) the nucleotide sequence set forth in SEQ ID NO: 1;

(b) a nucleotide sequence encoding the amino acid sequence set forth in SEQ ID NO: 2; and (c) the nucleotide sequence set forth in SEQ ID NO: 3.

2. The transgenic solanaceous plant or plant cell of claim 1, wherein the polynucleotide comprises the nucleotide sequence of (b) or (c) and further comprises a promoter operably linked for the expression of the nucleotide sequence in a plant.

3. The transgenic solanaceous plant or plant cell of claim 1, wherein the transgenic solanaceous plant or plant cell is a potato or tomato plant or plant cell.

4. A method for making a transgenic solanaceous plant or plant cell comprising enhanced resistance to a plant disease caused by *Phytophthora infestans*, the method comprising introducing a heterologous polynucleotide into at least one solanaceous plant cell, the heterologous polynucleotide comprising a nucleotide sequence selected from the group consisting of:

(a) the nucleotide sequence set forth in SEQ ID NO: 1;

(b) a nucleotide sequence encoding the amino acid sequence set forth in SEQ ID NO: 2; and (c) the nucleotide sequence set forth in SEQ ID NO: 3.

5. The method of claim 4, further comprising regenerating a solanaceous plant form the solanaceous cell, said regenerated plant comprising in its genome the polynucleotide.

6. The method of claim 4, wherein the polynucleotide comprises the nucleotide sequence of (b) or (c) and further comprises a promoter operably linked for the expression of the nucleotide sequence in a plant.

7. The method of claim 4, wherein the solanaceous plant is a potato or a tomato plant.

8. A solanaceous plant produced by the method of claim 4, or a fruit, tuber, leaf, or seed of the solanaceous plant, wherein the fruit, tuber, leaf or seed comprises the polynucleotide.

9. A method of limiting a plant disease caused by at least one race of at least one *Phytophthora* sp. in agricultural crop production, the method comprising planting a solanaceous seedling, tuber, or seed and growing the solanaceous seedling, tuber, or seed under conditions favorable for the growth and development of a solanaceous plant resulting therefrom, wherein the solanaceous seedling, tuber, or seed comprising stably incorporated in its genome a heterologous polynucleotide comprising a nucleotide sequence selected from the group consisting of:

(a) the nucleotide sequence set forth in SEQ ID NO: 1;

(b) a nucleotide sequence encoding the amino acid sequence set forth in SEQ ID NO: 2; and (c) the nucleotide sequence set forth in SEQ ID NO: 3.

10. The transgenic solanaceous plant or plant cell of claim 1, wherein the solanaceous plant or plant cell is selected from the group consisting of potato and tobacco.

* * * * *